US012173350B2

(12) United States Patent
Shabat et al.

(10) Patent No.: US 12,173,350 B2
(45) Date of Patent: Dec. 24, 2024

(54) CHEMILUMINESCENT PROBES FOR IMAGING/DETECTION OF PROTEASES

(71) Applicant: RAMOT AT TEL-AVIV UNIVERSITY LTD., Tel-Aviv (IL)

(72) Inventors: Doron Shabat, Tel-Aviv (IL); Michal Eli Roth-Konforti, Tel-Aviv (IL)

(73) Assignee: Ramot at Tel-Aviv University Ltd., Tel-Aviv (IL)

( * ) Notice: Subject to any disclaimer, the term of this patent is extended or adjusted under 35 U.S.C. 154(b) by 762 days.

(21) Appl. No.: 16/616,356

(22) PCT Filed: May 23, 2018

(86) PCT No.: PCT/IL2018/050557
§ 371 (c)(1),
(2) Date: Nov. 22, 2019

(87) PCT Pub. No.: WO2018/216012
PCT Pub. Date: Nov. 29, 2018

(65) Prior Publication Data
US 2020/0277647 A1 Sep. 3, 2020

Related U.S. Application Data

(60) Provisional application No. 62/557,881, filed on Sep. 13, 2017, provisional application No. 62/510,370, filed on May 24, 2017.

(51) Int. Cl.
| | |
|---|---|
| *C12Q 1/37* | (2006.01) |
| *C07K 5/062* | (2006.01) |
| *C07K 7/06* | (2006.01) |
| *C09K 11/06* | (2006.01) |
| *G01N 21/76* | (2006.01) |

(52) U.S. Cl.
CPC ............ *C12Q 1/37* (2013.01); *C07K 5/06052* (2013.01); *C07K 7/06* (2013.01); *C09K 11/06* (2013.01); *G01N 21/76* (2013.01); *C07K 2319/50* (2013.01); *C09K 2211/1007* (2013.01); *C09K 2211/1011* (2013.01); *C09K 2211/1018* (2013.01)

(58) Field of Classification Search
CPC ........ C12Q 1/37; C07K 5/06052; C07K 7/06; C07K 2319/50; C09K 11/06; C09K 2211/1007; C09K 2211/1011; C09K 2211/1018; G01N 21/76
See application file for complete search history.

(56) References Cited

U.S. PATENT DOCUMENTS 10,660,974 B2 * 5/2020 Shabat ................ C07F 9/65512
11,179,482 B2 * 11/2021 Shabat ...................... C07F 5/04
11,649,475 B2 * 5/2023 Shabat ..................... C12Q 1/14
435/14
11,931,429 B2 * 3/2024 Shabat ...................... C07F 5/04
2013/0078188 A1 3/2013 Tsien et al.

FOREIGN PATENT DOCUMENTS

| JP | 2011095273 A | 5/2011 |
| WO | 2012092373 A2 | 7/2012 |
| WO | 2012123916 A2 | 9/2012 |
| WO | 2017130191 A1 | 8/2017 |

OTHER PUBLICATIONS

Richard, Org & Biomol Chem, vol. 7(14), 2009, 2941-2957. (Year: 2009).*
Green, ACX Central Science, vol. 3(4), 2017, 349-358. (Year: 2017).*
Roth-Konforti, Angew Chem Int Ed, 2017, vol. 56, 15633-15638. (Year: 2017).*
Notification Concerning Transmittal of International Preliminary Report on Patentability and IPRP received in PCT/IL2018/050557 filed May 23, 2018, mailed Dec. 5, 2019.
Harris et al; "Effect of Pegylation on Pharmaceuticals" Nature Reviews. Drug Discovery, vol. 2, No. 3, pp. 214-221.(2003).
Griffin et al; "CelL-penetrating peptide CGKRK mediates efficient and widespread targeting of bladder mucosa following focal injury" Nanomedicine , Nanotechnology , Biology and Medicine, vol. 13, No. 6, pp. 1925-1932. (2017).
Tsuchikama et al; "Antibody-drug conjugates: recent advances in conjugation and linker chemistries", Protein & Cell, vol. 9, No. 1, pp. 33-46. (2018).
Elion-Shaffer et al.; "ortho-Chlorination of phenoxy 1,2-dioxetane yields superior chemiluminescent probes for in vitro and in vivo imaging"Organic & Biomolecular Chemistry, vol. 16, No. 10, pp. 1708-1712. (2018).
Extended European Search Report (EESR) received in European Patent Application No. 18804980.3 dated Feb. 2, 2021.
Weissleder et al : "In vivo imaging of tumors with protease-activated near-infrared fluorescent probes" nature biotechnology 17, pp. 375-378 (1999).
Oriana et al; "Synthesis of tri-functionalized MMP2 Fret probes using a chemo-selective and late-stage modification of unprotected peptides" Organic & Biomolecular Chemistry 15, 179. (2017).
Office Action in Japanese Application No. 2023-000803, issued Dec. 12, 2023. (2 pages).
Richard et al.; "Self-cleavable chemiluminescent probes suitable for protease sensing. Organic & biomolecular" chemistry, vol. 7, Issue 14, pp. 2941-2957. (2009).
Green et al.; "Opening a gateway for chemiluminescence cell imaging: Distinctive methodology for design of bright chemiluminescent dioxetane probes". ACS central science, vol. 3, Issue 4, pp. 349-358. (2017).

(Continued)

*Primary Examiner* — D Margaret M Seaman
(74) *Attorney, Agent, or Firm* — Knobbe, Martens, Olson & Bear, LLP

(57) ABSTRACT

The present invention provides turn-ON dioxetane-based chemiluminescence probes based on the Schapp's adamantylidene-dioxetane probe, which are capable of detecting or imaging, more specifically, determining the presence, or measuring the level, of proteases, as well as compositions and uses thereof.

22 Claims, 4 Drawing Sheets

Specification includes a Sequence Listing.

(56) References Cited

OTHER PUBLICATIONS

Roth-Konforti et al. "Unprecedented Sensitivity in a Probe for Monitoring Cathepsin B: Chemiluminescence Microscopy Cell-Imaging of a Natively Expressed Enzyme". Angewandte Chemie International Edition, vol. 56, Issue 49, pp. 15633-15638.( 2017).
Ryan et al.; "Ultrasensitive Chemiluminescent Detection of Cathepsin B: Insights into the New Frontier of Chemiluminescent Imaging". Angewandte Chemie International Edition, vol. 57, Issue 3, pp. 622-624. (2017).
Richard et al.; "Chemiluminescent probe for the in vitro detection of protease activity" Organic Letters 9(23), pp. 4853-4855. (2007).
International Search Report issued on Aug. 23, 2018. 4 pages.
Written Opinion issued on Aug. 23, 2018. 5 pages.
Richard et al., "Chemiluminescent Probe for the in Vitro Detection of Protease Activity", Organic Letters, 2007, in 3 pages.
Richard et al., "Chemiluminescent Probe for the in Vitro Detection of Protease Activity", Organic Letters, 2007, Supporting Information, in 25 pages.

* cited by examiner

CHEMILUMINESCENT PROBES FOR IMAGING/DETECTION OF PROTEASES

CROSS REFERENCE TO RELATED APPLICATIONS

This application is the U.S. National Phase under 35 U.S.C. § 371 of International Application No. PCT/IL2018/050557 filed May 23, 2018, designating the U.S. and published as WO 2018/216012 on Nov. 29, 2018, which claims the benefit of U.S. Provisional Application No. 62/510,370 filed May 24, 2017, and of U.S. Provisional Application No. 62/557,881 filed Sep. 13, 2017. Any and all applications for which a foreign or domestic priority claim is identified above and/or in the Application Data Sheet as filed with the present application are hereby incorporated by reference under 37 C.F.R. 1.57.

REFERENCE TO SEQUENCE LISTING

A Sequence Listing submitted as an ASCII text file via EFS-Web is hereby incorporated by reference in accordance with 35 U.S.C. § 1.52(e). The name of the ASCII text file for the Sequence Listing is SL_2_BEN9_012APC.TXT, the date of creation of the ASCII text file is May 13, 2022, and the size of the ASCII text file is 1.12 KB.

TECHNICAL FIELD

The present invention provides dioxetane-based chemiluminescence probes capable of detecting proteases, as well as compositions and uses thereof.

Abbreviations: ACN, acetonitrile; DCM, dichloromethane, DIPEA, diisopropylethylamine; DMF, N,N'-dimethylformamide; EEDQ, N-ethoxycarbonyl-2-ethoxy-1,2-dihydroquinoline; $Et_2O$, diethylether; $Et_3N$, triethylamine; EtOAc, ethylacetate; HBTU, 2-(1H-benzotriazol-1-yl)-1,1,3,3-tetramethyluronium hexafluorophosphate; HPLC, high pressure liquid chromatography; $K_2CO_3$, potassium carbonate; MeOH, methyl alcohol; $Na_2S_2O_3$, sodium thiosulfate; $Na_2SO_4$, sodium sulfate; $NH_4Cl$, ammonium chloride; PABA, p-aminobenzoic acid; PEG, polyethylene glycol; RLU, relative light units; RP-HPLC, reverse-phase high pressure liquid chromatography; TFA, trifluoroacetic acid; TIPS, triisopropylsilane; TLC, thin layer chromatography; TMS-Cl, trimethylsilyl chloride; 7HC, 7-hydroxycoumarin.

BACKGROUND ART

Proteases are a class of enzymes, which perform protein catabolism by hydrolysis of peptide bonds. Proteases have fundamental roles in numerous biological processes and are associated with a wide variety of pathological conditions, including cancer, arthritis, neurodegenerative and cardiovascular disorders. With strong evidence of protease involvement in diseases, proteases serve an important role in imaging and drug development. Cathepsin B, a lysosomal cysteine-protease is of significant importance as it is overexpressed in extracellular and pericellular matrix under pathological conditions, in many different cancer types including, e.g., breast, cervix, colon, colorectal, gastric, head and neck, liver, lung, melanoma, ovarian, pancreatic, prostate, and thyroid cancers. As such, a lot of effort has been put into developing molecular and medical imaging technologies, centering on protease activity in general, and cathepsin B activity in particular. Most of the development has revolved around optical imaging, directed at fluorescence imaging.

Although fluorescence imaging allows for sensitive monitoring, it has disadvantages, mostly due to auto-fluorescence leading to a low signal-to-noise ratio. Unlike fluorescence-based assays, chemiluminescence assays require no light excitation, resulting in added sensitivity and increased signal-to-noise ratio.

Amongst known chemiluminescence probes, Schaap's adamantylidene-dioxetane probes (Scheme 1, structure I) are with highest applicability, as they bear a stable dioxetane moiety, making them suitable for many chemical and biological conditions. As depicted in Scheme 1, Schaap's adamantylidene-dioxetane based chemiluminescence probe (structure I) is equipped with an analyte-responsive protecting group used to mask the phenol moiety of the probe. Removal of the protecting group by the analyte of interest generates an unstable phenolate-dioxetane species II, which decomposes through a chemiexcitation process to produce the excited intermediate benzoate ester III and adamantanone. The excited intermediate decays to its ground-state (benzoate ester IV) through emission of a blue light photon.

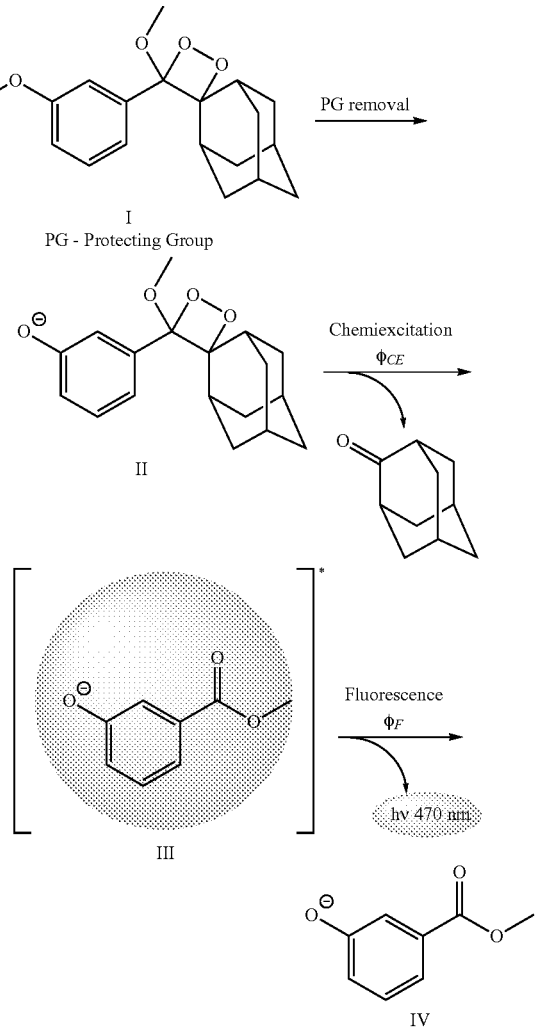

Scheme 1: Chemiluminescent activation pathway of Schaap's adamantylidene-dioxetane Richard et al. (2007) previously developed turn-ON chemiluminescence probes, bearing a protease (penicillin g-amidase or caspase-3) responsive substrate masking the phenol of the dioxetane luminophores. Although these probes show prominent signal-to-noise ratio, they prohibit live cell-imaging of proteases, as they require a two-step assay. First, the protease cleaves the protecting group in physiological pH (7.4) and then the mixture is added to a buffer with a pH of 12.3, which allows for the chemiexcitation process to occur.

International Publication No. WO 2017/130191 discloses chemiluminescence probes based on the Schapp's adamantylidene-dioxetane probe, wherein chemiluminescence emission is amplified through a direct mode of action, more particularly wherein the Schapp's adamantylidene-dioxetane probe is substituted at the ortho position of the phenolic ring with a π* acceptor group such as an acrylate and acrylonitrile electron-withdrawing group so as to increase the emissive nature of the benzoate species (Scheme 2). As shown in this publication, chemiluminescence probes as disclosed allow for the enzymatic hydrolysis and the chemiexcitation process to occur concurrently under physiological conditions, with remarkable chemiluminescence intensities.

Scheme 2: Direct chemiluminescence mode obtained by substituting the Schapp's adamantylidene-dioxetane probe at the ortho position of the phenolic ring with a π* acceptor group

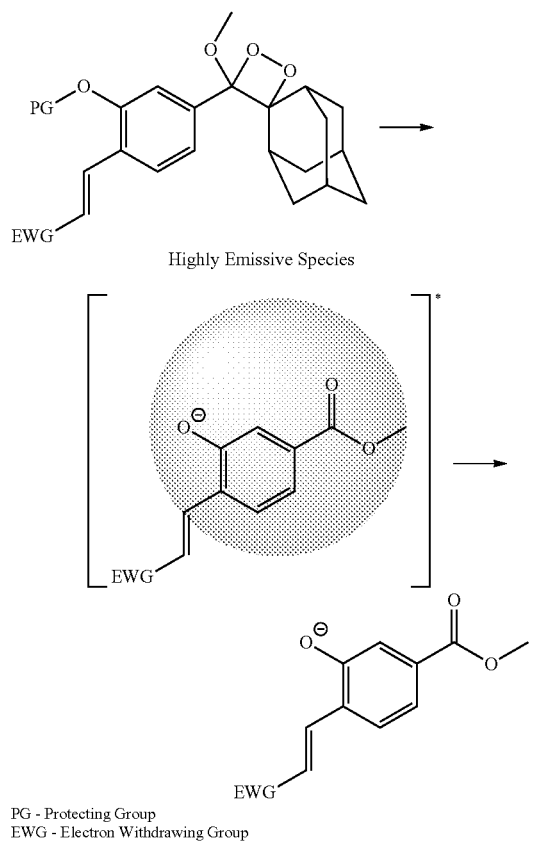

PG - Protecting Group
EWG - Electron Withdrawing Group

SUMMARY OF INVENTION

The present invention provides turn-ON dioxetane-based chemiluminescence probes based on those disclosed in the International Publication No. WO 2017/130191 and constructed with a protease cleavable substrate, which upon enzymatic degradation reveal dioxetane luminophores capable of emitting a chemiluminescent signal. The probes disclosed include a dioxetane luminophore that can be adapted with different halogens, changing the pKa of the luminophore, and an electron withdrawing group, yielding a donor-acceptor pair which gives a strong chemiliminescent signal, allowing for the probes to be used under aqueous conditions.

More particularly, in one aspect, the present invention provides a compound of the formula Ia or Ib:

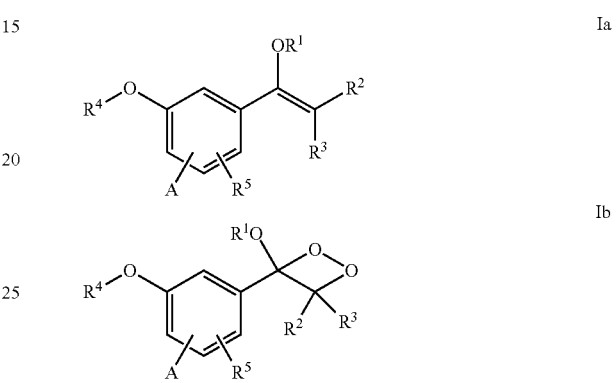

wherein
$R^1$ is selected from a linear or branched ($C_1$-$C_{18}$)alkyl, or ($C_3$-$C_7$)cycloalkyl;
$R^2$ and $R^3$ each independently is selected from a branched ($C_3$-$C_{18}$)alkyl or ($C_3$-$C7$)cycloalkyl, or $R_2$ and $R_3$ together with the carbon atom to which they are attached form a fused, spiro or bridged cyclic or polycyclic ring;
$R^4$ is a group of the formula:

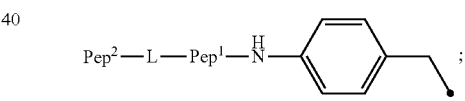

$R^5$ is H, or halogen attached either ortho or para to the —O—$R^4$ group;
A is a π* acceptor group of the formula —CH=CH-E, attached either ortho or para to the —O—$R^4$ group, wherein E is —CN, —COOH, —COO($C_1$-$C_{18}$)alkyl, 4-pyridinyl, methylpyridinium-4-yl, 3,3-dimethyl-3H-indolyl, or 1,3,3-trimethyl-3H-indol-1-ium-2-yl;
Pep$^1$ is a protease cleavable peptide moiety consisting of at least two amino acid residues and linked via a carboxylic group thereof to the aniline group, wherein said peptide moiety is optionally protected or linked, e.g., via an amide bond, through an amino group thereof to a PEG-containing group;
L is absent, or is a linker linked to Pep$^1$ via an amide bond through either a carboxyl or amino group of Pep$^1$; and
Pep$^2$ is absent, or a cell-penetrating peptide moiety linked to L either via an amide bond through an amino or carboxyl group thereof, or through a thiol group thereof,
provided that L and Pep$^2$ are both either absent or present, and when Pep$^1$ is protected or linked to a PEG-containing group, L and Pep$^2$ are absent.

In another aspect, the present invention provides a composition, e.g., a pharmaceutical composition, comprising a dioxetane-based chemiluminescence probe as disclosed herein, i.e., a compound of the formula Ia/Ib as defined above, and a carrier, e.g., a pharmaceutically acceptable carrier. The compounds and compositions of the invention may be used for imaging/detection of a protease such as a cathepsin, legumain, prostate specific antigen (PSA), and a metalloprotease, both in vitro and in vivo.

In a further aspect, the present invention thus relates to a dioxetane-based chemiluminescence probe as disclosed herein, i.e., a compound of the formula Ia/Ib as defined above, or a pharmaceutical composition comprising said compound, for use in vivo in diagnostics or imaging, more specifically, for determining the presence, or measuring the level, of a protease in vivo.

In yet another aspect, the present invention relates to a method for determining the presence, or measuring the level, of a protease in a sample, e.g., a biological sample such as a bodily fluid, a bodily fluid-based solution or a tissue biopsy sample, said method comprising (i) contacting said sample with a dioxetane-based chemiluminescence probe of the formula Ia/Ib as defined above wherein Pep$^1$ is a group cleavable by said protease, or a composition comprising said compound, to thereby hydrolyze said compound to an emissive species by said protease, when present in said sample; and (ii) detecting the chemiluminescence emission of said emissive species.

DETAILED DESCRIPTION

Figure 1A:
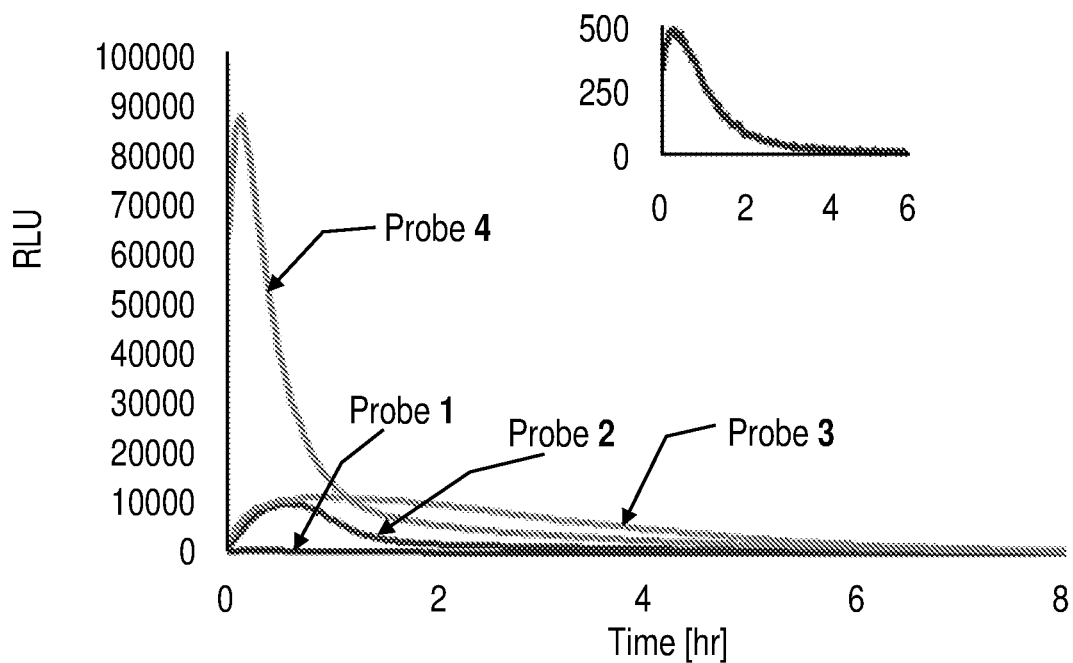
FIGS. 1A-1C show the chemiluminescence kinetic profiles of probes 1, 2, 3 and 4 [1 µM] in activity buffer (pH 7.4, 10% DMSO) in the presence of 2.5 units/mL cathepsin B at room temperature (1A; the inset focuses on the kinetic profile of probe 1); the total light emitted from each probe (1B); and the maximal signal yielded by each probe (1C).

In one aspect, the present invention provides a turn-ON dioxetane-based chemiluminescence probe, more specifically a compound of the formula Ia or Ib, as defined above.

The term "alkyl" typically means a linear or branched hydrocarbon radical having, e.g., 1-18 carbon atoms and includes methyl, ethyl, n-propyl, isopropyl, n-butyl, sec-butyl, isobutyl, tent-butyl, n-pentyl, isoamyl, 2,2-dimethylpropyl, n-hexyl, n-heptyl, n-octyl, n-nonyl, n-decyl, n-undecyl, n-dodecyl, n-tridecyl, n-tetradecyl, n-pentadecyl, n-hexadecyl, and the like. Preferred are ($C_1$-$C_8$)alkyl groups, more preferably ($C_1$-$C_4$)alkyl groups, most preferably methyl, ethyl, and isopropyl.

The term "alkylene" refers to a linear or branched divalent hydrocarbon radical derived after removal of hydrogen atom from an alkyl. Examples of alkylenes include, without being limited to, methylene, ethylene, propylene, butylene, 2-methylpropylene, pentylene, 2-methylbutylene, hexylene, 2-methylpentylene, 3-methylpentylene, 2,3-dimethylbutylene, heptylene, octylene, n-tridecanylene, n-tetradecanylene, n-pentadecanylene, n-hexadecanylene, n-heptadecanylene, n-octadecanylene, n-nonadecanylene, icosanylene, henicosanylene, docosanylene, tricosanylene, tetracosanylene, pentacosanylene, and the like. The term "alkylene chain" refers to a group of the formula —$(CH_2)_n$— derived after removal of two hydrogen atoms from a linear hydrocarbon of the formula $C_nH_{2n+2}$.

The term "cycloalkyl" means a mono- or bicyclic saturated hydrocarbyl group having, e.g., 3-7 carbon atoms such as cyclopropyl, cyclobutyl, cyclopentyl, cyclohexyl, cycloheptyl, and the like, that may be substituted, e.g., by one or more alkyl groups.

The term "halogen" as used herein refers to a halogen and includes fluoro, chloro, bromo, and iodo, but it is preferably fluoro or chloro.

The term "amino acid" as used herein refers to an organic compound comprising both amine and carboxylic acid functional groups, which may be either a natural or non-natural amino acid. The twenty-two amino acids naturally occurring in proteins are aspartic acid (Asp), tyrosine (Tyr), leucine (Leu), tryptophan (Trp), arginine (Arg), valine (Val), glutamic acid (Glu), methionine (Met), phenylalanine (Phe), serine (Ser), alanine (Ala), glutamine (Gin), glycine (Gly), proline (Pro), threonine (Thr), asparagine (Asn), lysine (Lys), histidine (His), isoleucine (Ile), cysteine (Cys), selenocysteine (Sec), and pyrrolysine (Pyl). Non-limiting examples of other amino acids include citrulline (Cit), diaminopropionic acid (Dap), diaminobutyric acid (Dab), ornithine (Orn), aminoadipic acid, β-alanine, 1-naphthylalanine, 3-(1-naphthyl)alanine, 3-(2-naphthyl)alanine, γ-aminobutiric acid (GABA), 3-(aminomethyl) benzoic acid, p-ethynyl-phenylalanine, p-propargly-oxy-phenylalanine, m-ethynyl-phenylalanine, p-bromophenylalanine, p-iodophenylalanine, p-azidophenylalanine, p-acetylphenylalanine, norleucine (Nle), azidonorleucine, 6-ethynyl-tryptophan, 5-ethynyl-tryptophan, 3-(6-chloroindolyl)alanine, 3-(6-bromoindolyl)alanine, 3-(5-bromoindolyl)alanine, azidohomoalanine, p-chlorophenylalanine, α-aminocaprylic acid, O-methyl-L-tyrosine, N-acetylgalactosamine-α-threonine, and N-acetylgalactosamine-α-serine.

The term "amino acid residue" as used herein refers to a residue of an amino acid after removal of hydrogen atom from an amino group thereof, e.g., its α-amino group or side chain amino group if present, and —OH group from a carboxyl group thereof, e.g., its α-carboxyl group or side chain carboxyl group if present.

The term "peptide" refers to a short chain of amino acid monomers (residues), e.g., a chain consisting of 2, 3, 4, 5, 6, 7, 8, 9, 10, 11, 12 or more amino acid residues, linked by peptide bonds, i.e., the covalent bond formed when a carboxyl group of one amino acid reacts with an amino group of another. The term "peptide moiety" as used herein refers to a moiety of a peptide as defined herein after removal of the hydrogen atom from a carboxylic group, i.e., either the terminal or a side chain carboxylic group, thereof, and/or a hydrogen atom from an amino group, i.e., either the terminal or a side chain amino group, thereof.

The term "peptide bond" or "amide bond" as used herein refers to the covalent bond —C(O)NH— formed between two molecules, e.g., two amino acids, when a carboxyl group of one of the molecules reacts with an amino group of the other molecule, causing the release of a molecule of water.

The term "amino protecting group" as used herein refers to any amino protecting group known in the art. An artisan skilled in the art can readily determine which protecting group(s) may be useful for the protection of the amino group(s), and standard methods are known in the art and are described in the literature. For example, suitable protecting groups are described in Green and Wuts, "*Protective Groups in Organic Synthesis*", John Wiley and Sons, Chapter 7, 1991. Preferred amino protecting groups include carbobenzyloxy (carboxybenzyl, Cbz), N-morpholinecarbonyl, p-methoxybenzyl carbonyl, tert-butyloxycarbonyl (Boc), 9-fluorenylmethyloxycarbonyl (Fmoc), acetyl, benzyl, a carbamate group, p-methoxybenzyl (PMB), 3,4-dimethoxybenzyl (DMPM), p- methoxyphenyl (PMP), and a tosyl group.

The term "π* acceptor group" as used herein refers to a group containing a π* acceptor system capable of accepting electrons, more specifically to a group of the formula —CH=CH-E, wherein E is —CN, —COOH, —COO($C_1$-$C_{18}$)alkyl, preferably —COO($C_1$-$C_8$)alkyl, more preferably —COO($C_1$-$C_4$)alkyl, 4-pyridinyl, methylpyridinium-4-yl, 3,3-dimethyl-3H-indolyl, or 1,3,3-trimethyl-3H-indol-1-ium-2-yl (see also Table 1).

TABLE 1

Certain π* acceptor groups A of the formula
—CH=CH—E (names refer to group E)

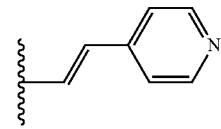

4-piridinyl

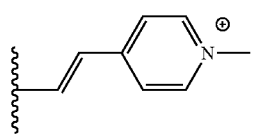

methylpiridinium-4-yl

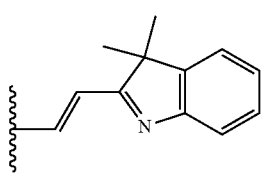

3,3-dimethyl-3H-indolyl

TABLE 1-continued

Certain π* acceptor groups A of the formula
—CH=CH—E (names refer to group E)

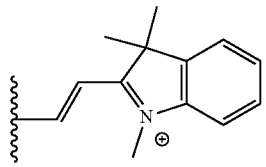

1,3,3-trimethyl-3H-indol-1-ium-2-yl

In certain embodiments, the invention provides a compound of the formula Ia or Ib, wherein $R^1$ is a linear or branched ($C_1$-$C_8$)alkyl, preferably ($C_1$-$C_4$)alkyl, more preferably methyl, ethyl, or isopropyl.

In certain embodiments, the invention provides a compound of the formula Ia or Ib, wherein $R^2$ and $R^3$ each independently is a branched ($C_3$-$C_{18}$)alkyl or ($C_3$-$C_7$)cycloalkyl. In other embodiments, $R^2$ and $R^3$ together with the carbon atom to which they are attached form a fused, spiro or bridged polycyclic ring. In a particular such embodiment, $R^2$ and $R^3$ together with the carbon atom to which they are attached form adamantyl.

In certain embodiments, the invention provides a compound of the formula Ia or Ib, wherein $R^5$ is halogen, e.g., Cl or F, attached ortho to the —O—$R^4$ group.

In certain embodiments, the invention provides a compound of the formula Ia or Ib, wherein A is —CH=CH-E attached ortho to the —O—$R^4$ group, wherein E is —CN, —COOH, —COO($C_1$-$C_8$)alkyl, e.g., —COO($C_1$-$C_4$)alkyl such as —COOCH$_3$, —COOC$_2$H$_5$, —COOC$_3$H$_7$, —COOCH(CH$_3$)$_2$, or —COOC(CH$_3$)$_3$, 4-pyridinyl, methylpyridinium-4-yl, 3,3-dimethyl-3H-indolyl, or 1,3,3-trimethyl-3H-indol-1-ium-2-yl. In particular such embodiments, E is —CN, —COOH, —COOCH$_3$, —COOC$_2$H$_5$, —COOC$_3$H$_7$, —COOCH(CH$_3$)$_2$, or —COOC(CH$_3$)$_3$.

In certain embodiments, the invention provides a compound of the formula Ia or Ib, wherein $R^1$ is a linear or branched ($C_1$-$C_8$)alkyl, preferably ($C_1$-$C_4$)alkyl, more preferably methyl, ethyl, or isopropyl; $R^2$ and $R^3$ together with the carbon atom to which they are attached form a fused, spiro or bridged polycyclic ring; $R^5$ is halogen attached ortho to the —O—$R^4$ group; and A is —CH=CH-E attached ortho to the —O—$R^4$ group, wherein E is —CN, —COOH, —COO($C_1$-$C_8$)alkyl, 4-pyridinyl, methylpyridinium-4-yl, 3,3-dimethyl-3H-indolyl, or 1,3,3-trimethyl-3H-indol-1-ium-2-yl. Particular such embodiments are those wherein $R^1$ is methyl; $R^2$ and $R^3$ together with the carbon atom to which they are attached form adamantyl; $R^5$ is halogen attached ortho to the —O—$R^4$ group; and E is —CN, —COOH, or —COO($C_1$-$C_4$)alkyl such as —COOCH$_3$, —COOC$_2$H$_5$, —COOC$_3$H$_7$, —COOCH(CH$_3$)$_2$, or —COOC(CH$_3$)$_3$. More particular such embodiments are those wherein E is —CN, —COOH, —COOCH$_3$, or —COOC(CH$_3$)$_3$, i.e., A is acrylonitrile, acrylic acid, methylacrylate or tert-butyl acrylate substituent, respectively, attached ortho to the —O—$R^4$ group.

As described above, the chemiluminescence probes of the present invention have a protease (also termed "peptidase" or "proteinase") cleavable peptide moiety (identified herein as Pep$^1$ that is part of the group $R^4$), i.e., a moiety of an amino acid sequence, optionally modified, that is cleavable by a protease, i.e., an enzyme capable of performing proteolysis (protein catabolism) by hydrolysis of peptide bonds, wherein removal of said cleavable group by the particular protease of interest generates an unstable phenolate-dioxetane species that decomposes through a chemiexcitation process to produce the excited intermediate, which then decays to its ground-state through emission of light.

The protease referred to throughout this specification may be any protease such as a serine protease, a cysteine protease, a threonine protease, an aspartic protease, a glutamic protease, or a metalloprotease, i.e., a protease enzyme whose catalytic mechanism involves a metal (usually zinc).

In certain embodiments, the protease referred to herein is a cathepsin such as cathepsin A or G (serine proteases); cathepsin B, C, F, H, K, L1, L2, O, S, W or Z (cysteine proteases); and cathepsin D or E (aspartyl protease).

In certain particular such embodiments, the chemiluminescence probe of the formula Ia/Ib is aimed at detecting the presence, more particularly over expression, of cathepsin B, a lysosomal cysteine protease involved in intracellular proteolysis, which is overexpressed in premalignant lesions and various pathological conditions, as well as in cancers, e.g., in tumor endothelial cells and many other tumor cells in the lysosome (Miller et al., 2009). Cathepsin B-cleavable peptides include, without limiting, peptides comprising, or consisting of, the amino acid sequence Val-Cit, Phe-Lys, or Gly-Phe-Leu-Gly (such peptides will be linked via the carboxylic group of the citrulline, lysine or glycine, respectively, to the aniline group of $R^4$).

In other particular such embodiments, the chemiluminescence probe of the formula Ia/Ib is aimed at detecting the presence, more particularly over expression, of cathepsin K, a lysosomal cysteine protease involved in bone remodeling and resorption, which is expressed predominantly in osteoclasts and overexpressed extracellularly in bone neoplasms (Segal et al., 2009). Cathepsin K-cleavable peptides include, without being limited to, peptides comprising the amino acid sequence Gly-Gly-Pro-Nle (such peptides will be linked via the carboxylic group of the norleucine to the aniline group of $R^4$).

In certain embodiments, the protease referred to herein is legumain, a lysosomal enzyme that is overexpressed in tumor cells (Stern et al., 2009), and the chemiluminescence probe of the formula Ia/Ib is aimed at detecting the presence, more particularly over expression, of said protease. Legumain-cleavable peptides include, without limiting, peptides comprising the amino acid sequence Ala-Ala-Asn (such peptides will be linked via the carboxylic group of the asparagine to the aniline group of $R^4$).

In certain embodiments, the protease referred to herein is PSA (also known as kallikrein-3), a member of the kallikrein-related protease family that is secreted by the epithelial cells of the prostate gland and used as a marker for prostate cancer or other prostate disorders, and the chemiluminescence probe of the formula Ia/Ib is aimed at detecting the presence, more particularly over expression, of said protease. PSA-cleavable peptides include, without being limited to, peptides comprising the amino acid sequence His-Ser-Ser-Lys-Leu-Gln (such peptides will be linked via the carboxylic group of the glutamine to the aniline group of $R^4$).

In certain embodiments, the protease referred to herein is a matrix metalloprotease (MMP), i.e., a family member of Zn-dependent endopeptidases that are collectively capable of hydrolyzing all proteins of the extracellular matrix, and thus play important roles in physiological processes such as tissue morphogenesis and repair. MMPs are also important contributors to cancer progression by promoting tumor cell invasion of the basement membrane and stroma, blood vessel penetration, and metastasis. Numerous studies have shown, e.g., that MMP9 is critical for the formation of the pre-metastatic niche and has a distinct role in tumor angiogenesis by regulating the bioavailability of vascular endothelial growth factor. Clinically, elevated levels of MMP9 correlate to tumor aggressiveness, stage and poor prognosis in a broad range of cancer types. Data have also been published with respect to MMP2.

In certain embodiments, the invention provides a compound of the formula Ia or Ib as defined in any one of the embodiments above, wherein $Pep^1$ is a protease cleavable peptide moiety comprising, or consisting of, the amino acid sequence Val-Cit, Phe-Lys, Gly-Phe-Leu-Gly, (SEQ ID NO: 1), Gly-Gly-Pro-Nle, (SEQ ID NO: 2), Ala-Ala-Asn or His-Ser-Ser-Lys-Leu-Gln (SEQ ID NO: 3), wherein said amino acid sequence is linked via the carboxylic group of the citrulline, lysine, glycine, norleucine, asparagine or glutamine, respectively, to the aniline group of $R^4$; and optionally protected at an amino group thereof, or linked via an amide bond and through said amino group to a PEG-containing group, e.g., a PEG-containing group of the formula:

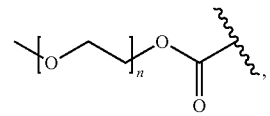

wherein n is an integer of 1 to 227.

In certain particular such embodiments, $Pep^1$ is a protease cleavable peptide moiety of the sequence Val-Cit, Phe-Lys, Gly-Phe-Leu-Gly, Gly-Gly-Pro-Nle, Ala-Ala-Asn or His-Ser-Ser-Lys-Leu-Gln, linked via the carboxylic group of the citrulline, lysine, glycine, norleucine, asparagine or glutamine, respectively, to the aniline group, and protected at the α-amino group of the valine, phenylalanine, glycine, glycine, alanine or histidine, respectively, with an amino protecting group, e.g., carboxybenzyl or N-morpholinecarbonyl.

In other particular such embodiments, $Pep^1$ is a protease cleavable peptide moiety of the sequence Val-Cit, Phe-Lys, Gly-Phe-Leu-Gly, Gly-Gly-Pro-Nle, Ala-Ala-Asn or His-Ser-Ser-Lys-Leu-Gln, linked via the carboxylic group of the citrulline, lysine, glycine, norleucine, asparagine or glutamine, respectively, to the aniline group, and linked via the α-amino group of the valine, phenylalanine, glycine, glycine, alanine or histidine, respectively, to a PEG-containing group of the formula:

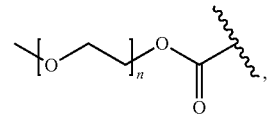

wherein n is an integer of 1 to 227.

In certain embodiments, the invention provides a compound of the formula Ia or Ib as defined in any one of the embodiments above, wherein $Pep^1$ is a protease cleavable peptide moiety comprising, or consisting of, the amino acid sequence Val-Cit, Phe-Lys, Gly-Phe-Leu-Gly, (SEQ ID NO: 1), Gly-Gly-Pro-Nle (SEQ ID NO: 2), Ala-Ala-Asn or His-Ser-Ser-Lys-Leu-Gln, (SEQ ID NO: 3), linked via the carboxylic group of the citrulline, lysine, glycine, norleucine, asparagine or glutamine, respectively, to the aniline group; L is a linker linked to Pep¹ via an amide bond through either a carboxyl or amino group of Pep¹; and Pep² is a cell-penetrating and solubilizing peptide moiety linked to L through a thiol group thereof. In particular such embodiments, L is a linker of the formula:

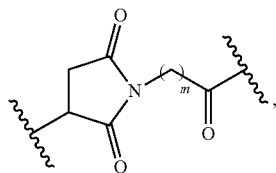

linked to Pep¹ via an amide bond through an amino group of Pep¹, wherein m is an integer of 1-20, and the alkylene chain of L is optionally interrupted with one or more —O— groups; and Pep² is a cell-penetrating and solubilizing peptide moiety, e.g., a peptide moiety of the sequence Cys-Gly-Lys-Arg-Lys (SEQ ID NO: 4), linked to L through the thiol group of the cysteine residue.

In specific embodiments, the compound disclosed herein is a compound of the formula Ia or Ib, wherein R¹ is methyl; R² and R³ together with the carbon atom to which they are attached form adamantyl; R⁵ is Cl attached ortho to the —O—R⁴ group; A is —CH=CH-E attached ortho to the —O—R⁴ group; E is —COOCH₃ or —CN; and (i) Pep¹ is a peptide moiety of the sequence Val-Cit, linked via the carboxylic group of the citrulline to the aniline group, and protected at the amino group of the valine with carboxybenzyl (e.g., compounds Ib-1a and Ib-1b in Table 2); (ii) Pep¹ is a peptide moiety of the sequence His-Ser-Ser-Lys-Leu-Gln, linked via the carboxylic group of the glutamine to the aniline group, and protected at the α-amino group of the histidine with N-morpholinecarbonyl (e.g., compounds Ib-2a and Ib-2b in Table 2); (iii) Pep¹ is a peptide moiety of the sequence Val-Cit, linked via the carboxylic group of the citrulline to the aniline group, and linked via the amino group of the valine to a PEG-containing group of the formula

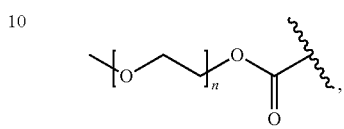

wherein n is 17 (e.g., compounds Ib-3a and 3b-1b in Table 2); or (iv) Pep¹ is a peptide moiety of the sequence Val-Cit or His-Ser-Ser-Lys-Leu-Gln, linked via the carboxylic group of the citrulline or glutamine, respectively, to the aniline group; L is a linker of the formula:

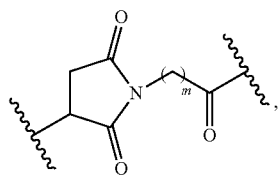

wherein m is an integer of 5, linked to Pep¹ via an amide bond through the α-amino group of the valine or histidine, respectively; and Pep² is a peptide moiety of the sequence Cys-Gly-Lys-Arg-Lys, linked to L through the thiol group of the cysteine residue (e.g., compounds Ib-4a, Ib-4b, Ib-5a and Ib-5b in Table 2).

TABLE 2

Specific compounds of the formula Ia/Ib disclosed herein

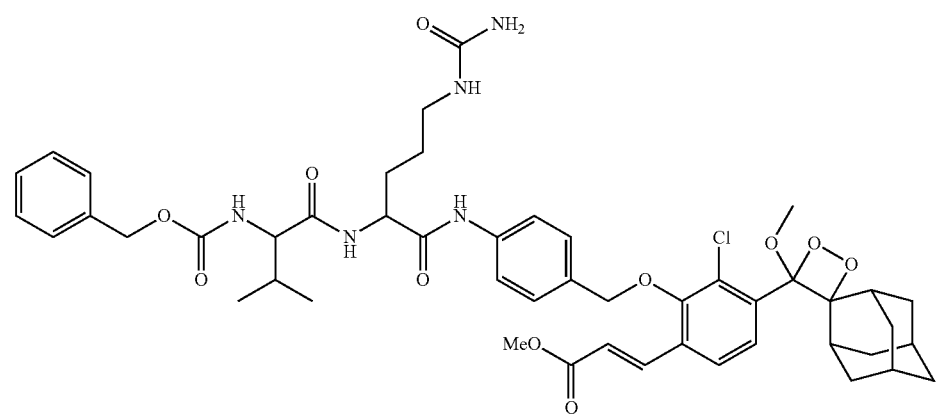 [SMILES: COC(=O)/C=C/c1ccc(C2(OC)OOC23C2CC4CC(C2)CC3C4)c(Cl)c1OCc1ccc(NC(=O)C(CCCNC(N)=O)NC(=O)C(NC(=O)OCc2ccccc2)C(C)C)cc1]

Ib-1a

TABLE 2-continued
Specific compounds of the formula Ia/Ib disclosed herein
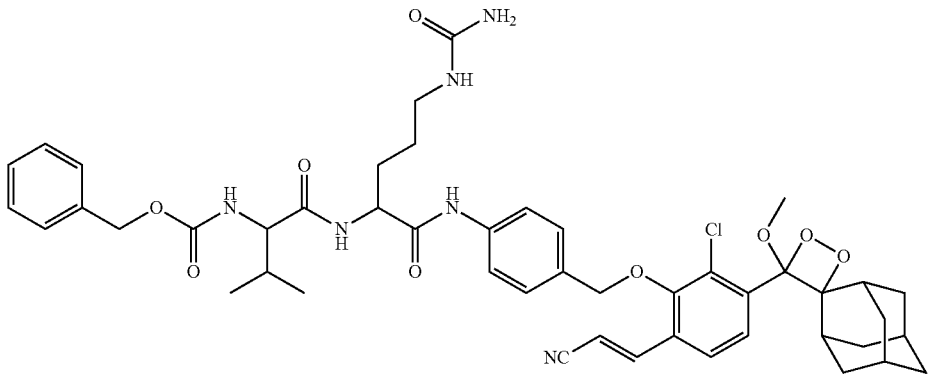 [SMILES: COC1(c2ccc(/C=C/C#N)c(OCc3ccc(NC(=O)C(CCCNC(N)=O)NC(=O)C(NC(=O)OCc4ccccc4)C(C)C)cc3)c2Cl)OOC12C1CC3CC(C1)CC2C3]
Ib-1b
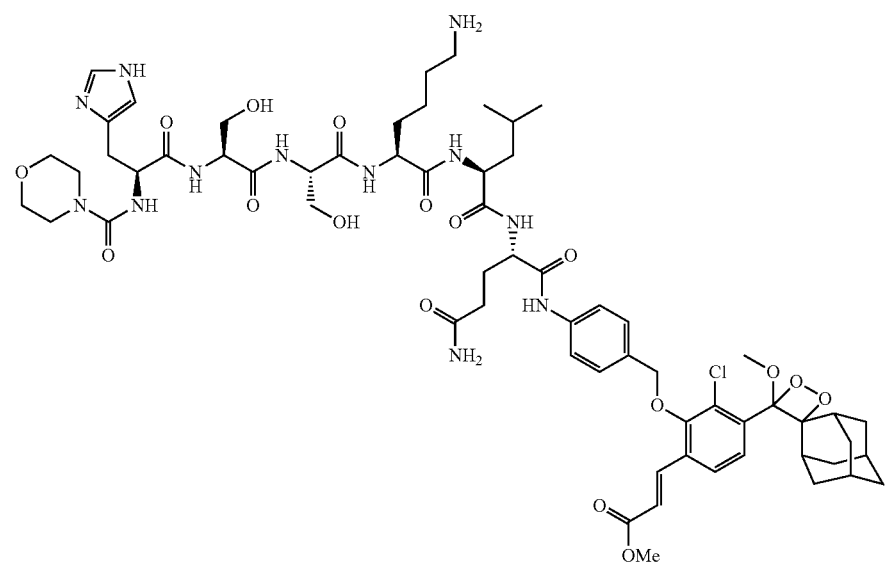 [SMILES: COC(=O)/C=C/c1ccc(C2(OC)OOC23C2CC4CC(C2)CC3C4)c(Cl)c1OCc1ccc(NC(=O)[C@H](CCC(N)=O)NC(=O)[C@H](CC(C)C)NC(=O)[C@H](CCCCN)NC(=O)[C@H](CO)NC(=O)[C@H](CO)NC(=O)[C@H](Cc2c[nH]cn2)NC(=O)N2CCOCC2)cc1]
Ib-2a
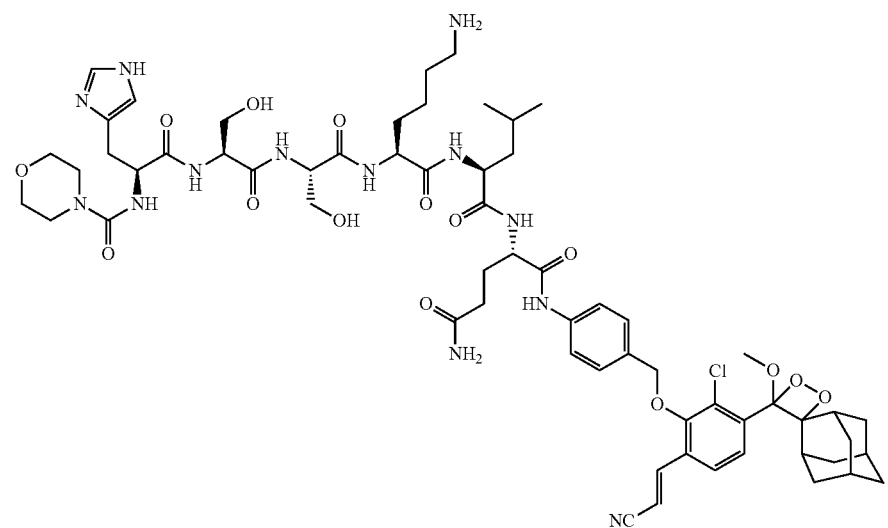 [SMILES: COC1(c2ccc(/C=C/C#N)c(OCc3ccc(NC(=O)[C@H](CCC(N)=O)NC(=O)[C@H](CC(C)C)NC(=O)[C@H](CCCCN)NC(=O)[C@H](CO)NC(=O)[C@H](CO)NC(=O)[C@H](Cc4c[nH]cn4)NC(=O)N4CCOCC4)cc3)c2Cl)OOC12C1CC3CC(C1)CC2C3]
Ib-2b TABLE 2-continued
Specific compounds of the formula Ia/Ib disclosed herein
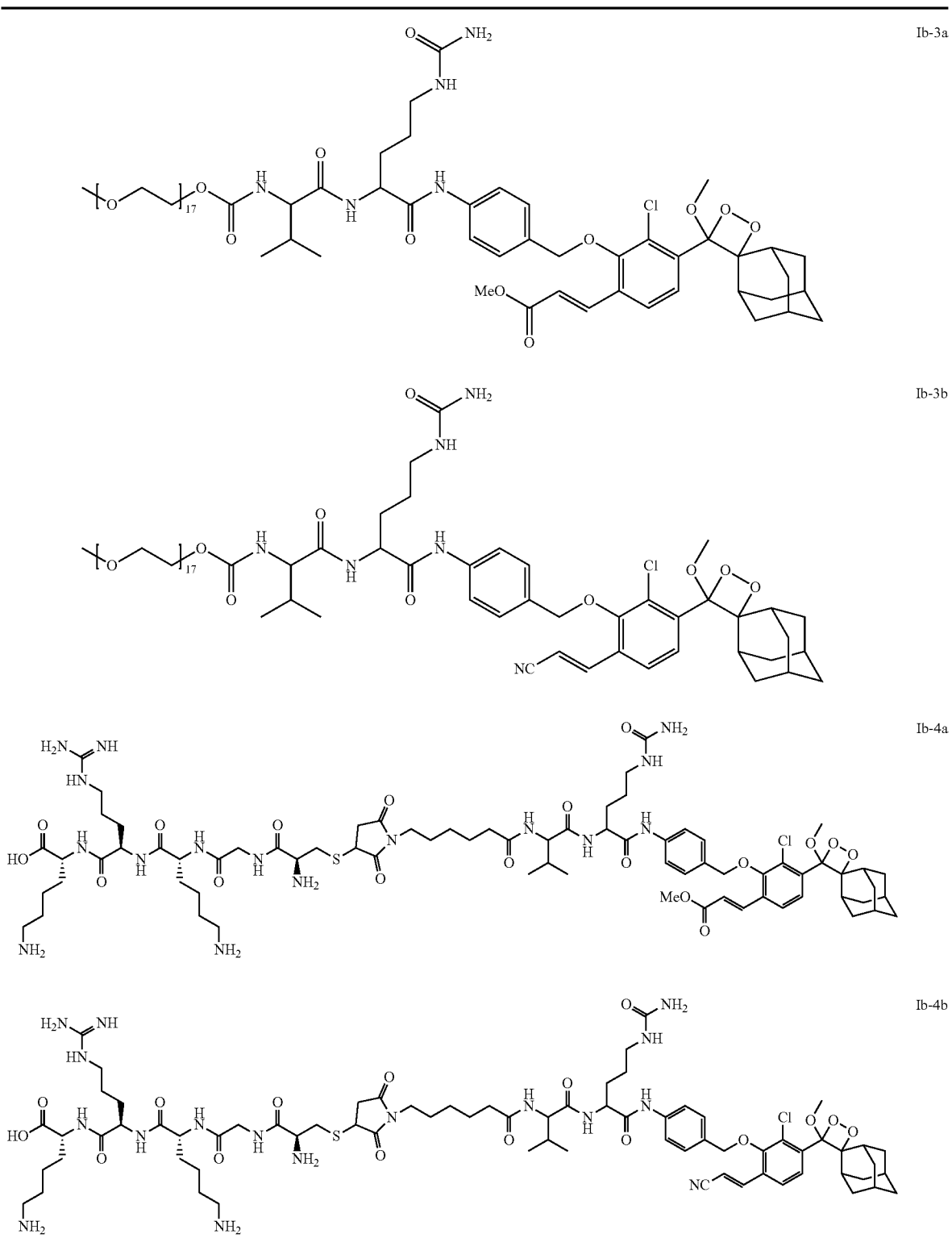

TABLE 2-continued

Specific compounds of the formula Ia/Ib disclosed herein

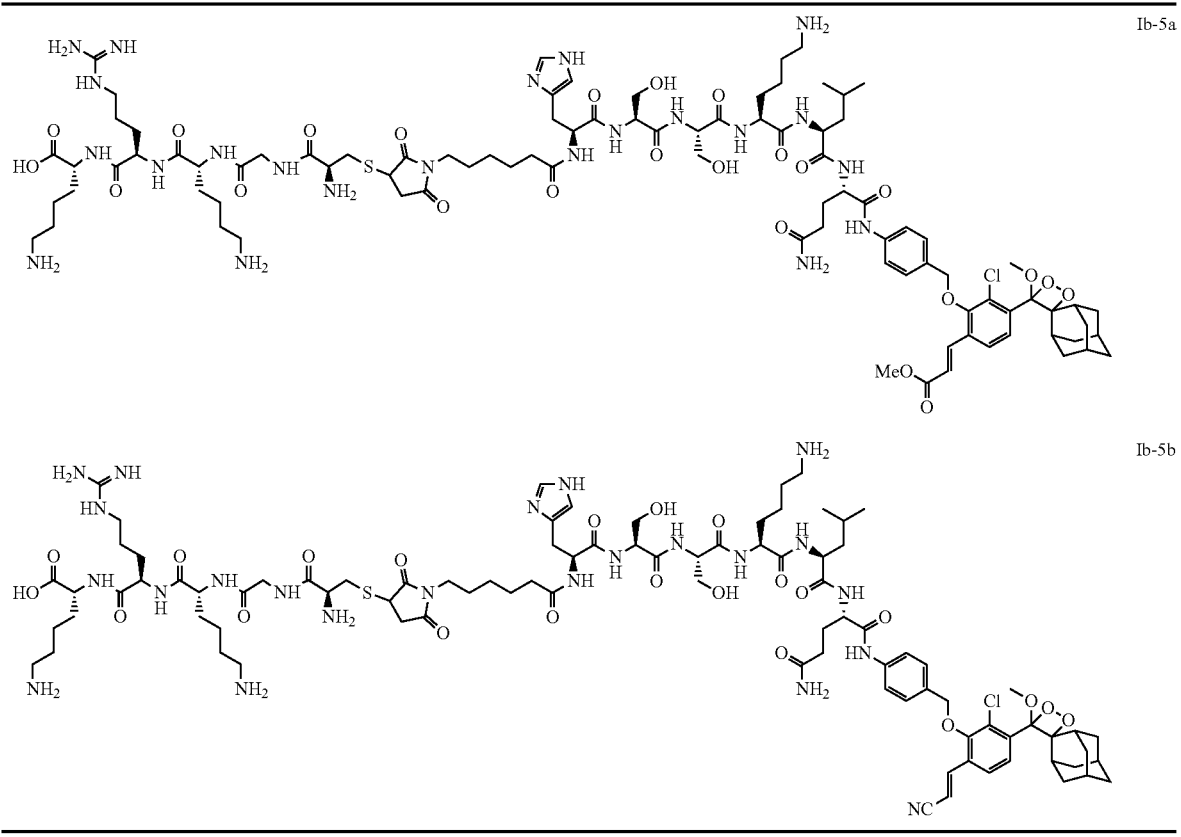

In another aspect, the present invention provides a composition comprising a dioxetane-based chemiluminescence probe as disclosed herein, i.e., a compound of the formula Ia/Ib as defined in any one of the embodiments above, and a carrier. Particular such compositions are pharmaceutical compositions comprising said chemiluminescence probe and a pharmaceutically acceptable carrier.

In specific embodiments, the composition of the present invention comprises a chemiluminescence probe of the formula Ia/Ib selected from those listed in Table 2.

The chemiluminescence probe of the formula Ia/Ib may be used for diagnostics and/or in vivo imaging, more specifically, for determining the presence, or measuring the level, of a protease such as a serine protease, a cysteine protease, a threonine protease, an aspartic protease, a glutamic protease, or a metalloprotease. Examples of such proteases include, without limiting, cathepsins such as cathepsin A, B, C, D, E, F, G, H, K, L1, L2, O, S, W and Z, legumain, and PSA.

In a further aspect, the present invention thus relates to (i) a dioxetane-based chemiluminescence probe of the formula Ia/Ib as defined in any one of the embodiments above; or (ii) a pharmaceutical composition comprising said chemiluminescence probe, for use in vivo in diagnostics or imaging, i.e., for determining the presence, or measuring the level, of a protease as defined above in vivo.

In other words, the present invention relates to a method for determining the presence, or measuring the level, of a protease as defined above in an individual in need, said method comprising (i) administering to said individual a compound of the formula Ia/Ib as defined in any one of the embodiments above, or a composition comprising said compound, to thereby hydrolyze said compound to an emissive species by said protease, when present in said individual; and (ii) detecting the chemiluminescence emission of said emissive species. According to the present invention, the chemiluminescence probe can be administered systemically or locally, e.g., to a particular organ of said individual, so as to determine the presence, or measure the level, of said protease in the whole body of said individual, or in said particular organ.

In yet another aspect, the present invention relates to a method for determining the presence, or measuring the level, of a protease in a sample, i.e., in vitro, said method comprising (i) contacting said sample with a compound of the formula Ia/Ib as defined in any one of the embodiments above wherein Pep$^1$ is a group cleavable by said protease, or a composition comprising said compound, to thereby hydrolyze said compound to an emissive species by said protease, when present in said sample; and (ii) detecting the chemiluminescence emission of said emissive species.

The sample analyzed according to this method may be any sample, e.g., a biological sample. The term "biological sample" as used herein refers to a tissue biopsy sample; a bodily fluid such as an amniotic fluid, aqueous humour, vitreous humour, bile, blood serum, breast milk, cerebrospinal fluid, cerumen (earwax), endolymph, perilymph, female ejaculate, gastric juice, mucus, peritoneal fluid, saliva, sebum (skin oil), semen, sweat, tears, vaginal secretion, vomit and urine; or a bodily fluid-based solution, i.e., an aqueous solution in which a bodily fluid is dissolved.

Pharmaceutical compositions according to the present invention may be prepared by conventional techniques, e.g., as described in Remington: The Science and Practice of Pharmacy, 19th Ed., 1995. The compositions can be prepared, e.g., by uniformly and intimately bringing the active agent, i.e., the dioxetane-based chemiluminescence probe disclosed herein, into association with a liquid carrier, a finely divided solid carrier, or both, and then, if necessary, shaping the product into the desired formulation. The compositions may be in liquid, solid or semisolid form and may further include pharmaceutically acceptable fillers, carriers, diluents or adjuvants, and other inert ingredients and excipients. In one embodiment, the pharmaceutical composition of the present invention is formulated as nanoparticles.

A pharmaceutical composition according to the present invention can be formulated for any suitable route of administration, e.g., for parenteral administration such as intravenous, intraarterial, intrathecal, intrapleural, intratracheal, intraperitoneal, intramuscular or subcutaneous administration, topical administration, oral or enteral administration, or for inhalation. In particular embodiments, such a composition is formulated for intravenous or intraperitoneal administration, or for subcutaneous administration.

The pharmaceutical composition of the invention may be in the form of a sterile injectable aqueous or oleaginous suspension, which may be formulated according to the known art using suitable dispersing, wetting or suspending agents. The sterile injectable preparation may also be a sterile injectable solution or suspension in a non-toxic parenterally acceptable diluent or solvent. Acceptable vehicles and solvents that may be employed include, e.g., water, Ringer's solution and isotonic sodium chloride solution.

The chemiluminescence emission of the probes of the present invention can be detected utilizing any technique or procedure known in the art.

Optical molecular imaging is a promising technique that provides a high degree of sensitivity and specificity in tumor margin detection. Furthermore, existing clinical applications have proven that optical molecular imaging is a powerful intraoperative tool for guiding surgeons performing precision procedures, thus enabling radical resection and improved survival rates. An example of a clinically approved instrument for minimally invasive surgical procedures under fluorescence guidance is the da Vinci Surgical System (Haber et al., 2010). This instrument is featured with a 3D HD vision system for a clear and magnified view inside a patient's body and allows surgeons to perform complex and routine procedures through a few small openings, similar to traditional laparoscopy. In addition, the following systems have already been applied in surgeries for breast cancer, liver metastases and bypassing graft surgery: The Hamamatsu's Photodynamic Eye (PDE™), Artemis™ and Novadaq SPY™ (Novadaq Technologies Inc., Toronto, Canada) (Chi et al., 2014). Several existing intraoperative NIR fluorescence molecular imaging systems were evaluated in clinical trials; including, Fluobeam®, FLARE™ and GXMI Navigator. They have played an important role in operation convenience, improving image assessment and increasing detection depth (Chi et al., 2014).

In recent years, there has been a great progress in the development of cameras and lasers for optical fluorescence imaging in the IR range (Mieog et al., 2011; Troyan et al., 2009). In parallel, there is a vast clinical use of low MW organic dyes such as ICG and methylene blue for determining cardiac output, hepatic function and liver blood flow, and for ophthalmic angiography. In 2015, the fluorescence imaging system, Xiralite®, gained FDA approval for visualization of microcirculation in the hands (for inflammation and perfusion-related disorders).

The invention will now be illustrated by the following non-limiting Examples.

EXAMPLES

Experimental

General Methods

All reactions requiring anhydrous conditions were performed under an argon atmosphere. All reactions were carried out at room temperature unless stated otherwise. Chemicals and solvents were either A.R. grade or purified by standard techniques. TLC: silica gel plates Merck 60 $F_{254}$: compounds were visualized by irradiation with UV light. Column chromatography (FC): silica gel Merck 60 (particle size 0.040-0.063 mm), eluent given in parentheses. RP-HPLC: C18 5u, 250×4.6 mm, eluent given in parentheses. Preparative RP-HPLC: C18 5u, 250×21 mm, eluent given in parentheses. $^1$H-NMR spectra were measured using Bruker Avance operated at 400 MHz. $^1$C-NMR spectra were measured using Bruker Avance operated at 100 MHz. Chemical shifts were reported in ppm on the δ scale relative to a residual solvent (CDCl3: δ=7.26 for 1H-NMR and 77.16 for 13C-NMR, DMSO-d6: δ=2.50 for 1H-NMR and 39.52 for 13C-NMR). Mass spectra were measured on Waters Xevo TQD. Chemiluminescence was recorded on Molecular Devices Spectramax i3x. All general reagents, including salts and solvents, were purchased from Sigma-Aldrich. Light irradiation for photochemical reactions: LED PAR38 lamp (19 W, 3000K).

Synthesis of Probe 1

Compound Ib. As depicted in Scheme 3, compound 1a (Dubowchik et al., 2002) (300 mg, 0.58 mmol, 1 eq) was dissolved in 7 mL of ACN and cooled to 0° C. Sodium iodide (264 mg, 1.76 mmol, 3 eq) was added followed by the rapid addition of TMS—Cl (222 μl, 1.76 mmol, 3 eq). The reaction was allowed to warm up to room temperature and monitored by TLC (MeOH:DCM 10:90). Upon completion, the reaction mixture was diluted with EtOAc, and washed with saturated $Na_2S_2O_3$ followed by brine. The organic layer was separated, dried over $Na_2SO_4$, filtered and the solvent was evaporated under reduced pressure, to afford compound 1b (245 mg, 67% yield) as an off-white solid. The compound was reacted without further purification. MS (ES+): m/z calc. for $C_{26}H_{34}IN_5O_5$: 623.16; found: 624.4 [M+H]$^+$.

Scheme 3: Synthesis of compound 1b

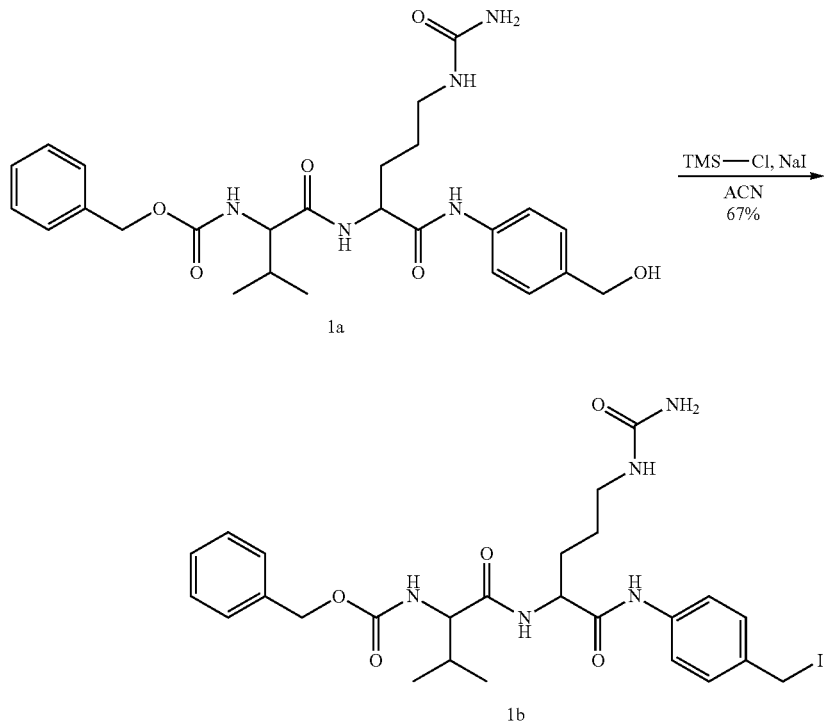

Probe 1. As depicted in Scheme 4, compound 1b (69 mg, 0.115 mmol, 1 eq) and compound 1c (Green et al., 2017) (37 mg, 0.127 mmol, 1.1 eq) were dissolved in 0.5 mL DMF and $K_2CO_3$ (35 mg, 0.253 mmol, 2.2 eq) was added. The reaction was monitored by TLC (MeOH:DCM 10:90). After completion, the reaction mixture diluted with EtOAc and was washed with saturated $NH_4Cl$. The organic layer was separated, washed with brine, dried over $Na_2SO_4$, filtered and the solvent was evaporated under reduced pressure. The crude product was reacted without further purification. MS (ES+): m/z calc. for $C_{44}H_{54}ClN_5O_7$: 799.37; found: 800.5 $[M+H]^+$.

The crude was dissolved in 5 mL DCM and a few drops of DMF (to enhance solubility). A few milligrams of methylene blue were added and oxygen was bubbled through the solution, while irradiating with yellow light. The reaction was monitored by RP-HPLC (50-100% ACN in water, 20 min). Upon completion, the reaction mixture was concentrated by evaporation under reduced pressure and the crude product was purified by preparative RP-HPLC (50-100% ACN in water, 20 min) to afford probe 1 (20 mg, 21% yield) as a white solid. MS (ES+): m/z calc. for $C_{44}H_{54}ClN_5O_9$: 831.36; found: 854.5 $[M+Na]^+$. $^1$H NMR (400 MHz, DMSO) δ 10.07 (s, 1H), 8.10 (d, J=7.6 Hz, 1H), 7.60 (d, J=8.5 Hz, 2H), 7.54 (d, J=7.7 Hz, 1H), 7.44 (t, J=8.0 Hz, 1H), 7.41-7.25 (m, 7H), 5.97 (s, 1H), 5.74 (s, 1H), 5.41 (s, 2H), 5.16 (q, J=12.0 Hz, 2H), 5.02 (s, 2H), 4.40 (dd, J=13.4, 7.9 Hz, 1H), 3.95-3.86 (m, 1H), 3.07 (s, 3H), 3.05-2.97 (m, 1H), 2.92 (dd, J=13.0, 6.1 Hz, 1H), 2.85 (s, 1H), 2.24 (d, J=12.8 Hz, 1H), 2.03-1.86 (m, 2H), 1.75-1.49 (m, 9H), 1.37 (dd, J=37.8, 8.8 Hz, 3H), 1.28-1.12 (m, 4H), 0.86 (d, J=6.8 Hz, 3H), 0.82 (d, J=6.7 Hz, 3H). $^{13}$C NMR (101 MHz, DMSO) δ 171.77, 171.17, 159.42, 156.68, 155.07, 139.27, 137.62, 132.84, 131.60, 128.87, 128.29, 128.17, 125.05, 120.70, 119.55, 116.55, 112.02, 95.77, 70.85, 65.92, 60.59, 53.58, 49.75, 36.46, 33.76, 33.48, 32.25, 31.62, 31.31, 30.90, 30.00, 27.31, 26.05, 25.72, 19.74, 18.68.

Scheme 4: Synthesis of chemiluminescence probe 1

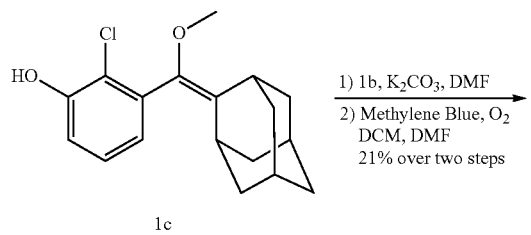

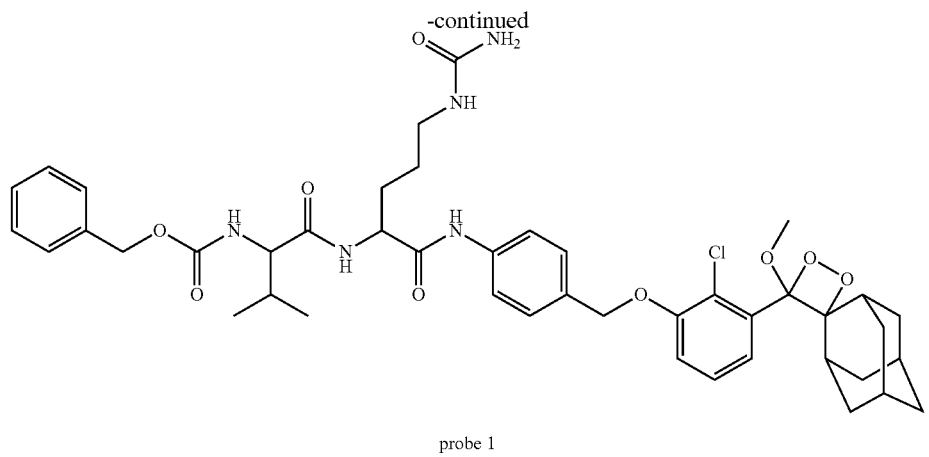

probe 1

Synthesis of Probe 2

Compound 2b. As depicted in Scheme 5, compound 1b (50 mg, 0.08 mmol, 1 eq) and compound 2a (Green et al., 2017) (34 mg, 0.09 mmol, 1.1 eq) were dissolved in 0.5 mL DMF and K$_2$CO$_3$ (24 mg, 0.18 mmol, 2.2 eq) was added. The reaction was monitored by TLC (MeOH:DCM 10:90). After completion, the reaction mixture diluted with EtOAc and was washed with saturated NH$_4$Cl. The organic layer was separated, washed with brine, dried over Na$_2$SO$_4$, filtered and the solvent was evaporated under reduced pressure. The crude product was purified by column chromatography on silica gel (MeOH:DCM 10:90) to afford compound 2b (29 mg, 41% yield) as a yellowish solid. MS (ES+): m/z calc. for C$_{48}$H$_{58}$ClN$_5$O$_9$: 883.39; found: 884.8 [M+H]$^+$. $^1$H NMR (400 MHz, CDCl3) δ 7.83 (d, J=16.2 Hz, 1H), 7.53 (d, J=8.2 Hz, 2H), 7.35 (t, J=8.5 Hz, 3H), 7.30-7.18 (m, 5H), 7.00 (d, J=8.0 Hz, 1H), 6.36 (d, J=16.2 Hz, 1H), 5.02 (q, J=12.3 Hz, 3H), 4.87 (d, J=3.1 Hz, 2H), 4.49 (dd, J=8.8, 4.9 Hz, 1H), 3.96 (d, J=6.2 Hz, 1H), 3.71 (s, 3H), 3.25 (s, 3H), 3.22-2.98 (m, 4H), 2.06-1.94 (m, 3H), 1.92-1.80 (m, 6H), 1.80-1.70 (m, 5H), 1.70-1.56 (m, 5H), 1.46 (s, 3H), 0.88 (d, J=6.7 Hz, 3H), 0.84 (d, J=6.8 Hz, 3H). $^{13}$C NMR (101 MHz, CDCl$_3$) δ 172.55, 170.37, 167.50, 157.00, 153.69, 139.29, 139.04, 138.32, 138.26, 138.20, 138.12, 136.17, 132.78, 131.83, 129.61, 128.51, 128.18, 127.88, 125.15, 119.91, 119.74, 75.82, 67.07, 60.48, 57.26, 53.16, 51.84, 39.13, 38.59, 36.99, 32.94, 31.00, 29.72, 29.29, 28.31, 25.99, 19.17, 17.79.

Scheme 5: Synthesis of compound 2b

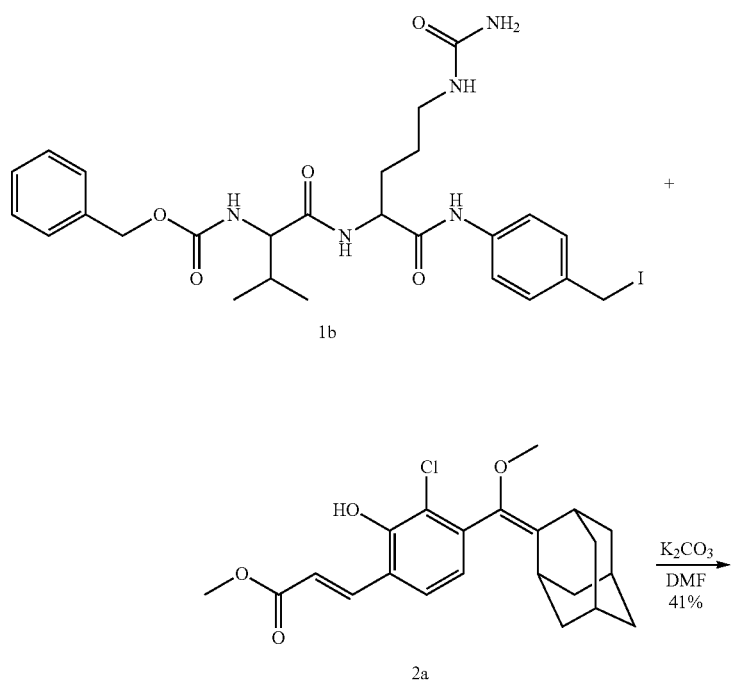

-continued

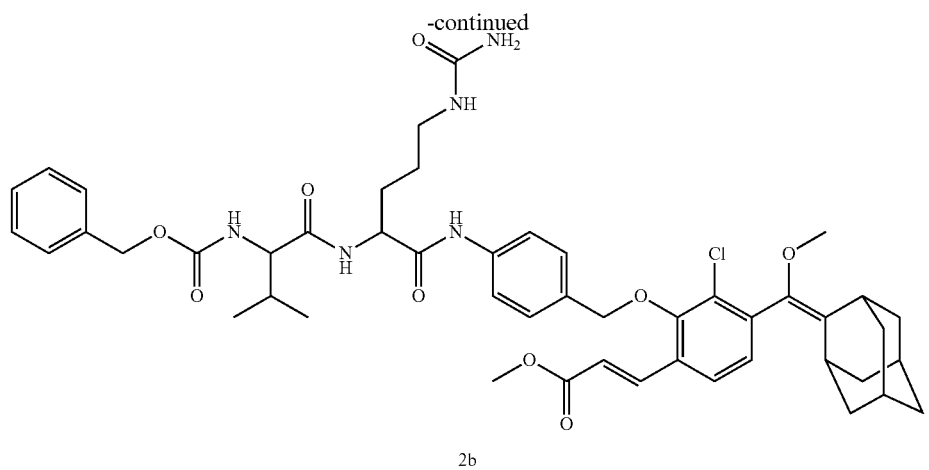

2b

Probe 2. As depicted in Scheme 6, compound 2b (20 mg, 0.02 mmol) was dissolved in 5 mL DCM and a few drops of DMF (to enhance solubility). A few milligrams of methylene blue were added and oxygen was bubbled through the solution, while irradiating with yellow light. The reaction was monitored by RP-HPLC (50-100% ACN in water, 20 min). Upon completion, the reaction mixture was concentrated by evaporation under reduced pressure and the crude product was purified by preparative RP-HPLC (50-100% ACN in water, 20 min) to afford probe 2 (8 mg, 40% yield) as a white solid. MS (ES−): m/z calc. for $C_{48}H_{58}ClN_5O_{11}$: 915.38; found: 950.6 [M+Cl]⁻. $^1$H NMR (400 MHz, DMSO) δ 10.09 (s, 1H), 8.11 (d, J=7.6 Hz, 1H), 7.94 (d, J=8.4 Hz, 1H), 7.77 (d, J=8.4 Hz, 1H), 7.71 (d, J=16.2 Hz, 1H), 7.60 (d, J=8.5 Hz, 2H), 7.37-7.27 (m, 6H), 6.67 (d, J=16.2 Hz, 1H), 5.98 (s, 1H), 5.42 (s, 1H), 5.02 (s, 2H), 4.92-4.85 (m, 2H), 4.41 (dd, J=13.4, 8.0 Hz, 1H), 3.96-3.85 (m, 1H), 3.71 (s, 3H), 3.10 (s, 3H), 2.98 (d, J=23.1 Hz, 2H), 2.87 (s, 1H), 2.22 (d, J=12.4 Hz, 1H), 1.96 (dd, J=13.5, 6.7 Hz, 1H), 1.89 (s, 1H), 1.77-1.48 (m, 11H), 1.49-1.11 (m, 7H), 0.86 (d, J=6.8 Hz, 3H), 0.82 (d, J=6.7 Hz, 3H). $^{13}$C NMR (101 MHz, DMSO) δ 171.79, 171.22, 166.73, 159.43, 156.69, 154.23, 139.86, 137.90, 137.62, 134.85, 131.79, 130.73, 130.20, 128.87, 128.30, 128.19, 127.39, 126.56, 121.77, 119.39, 111.72, 95.95, 76.26, 65.93, 60.59, 53.60, 52.24, 49.95, 39.83, 39.62, 39.41, 36.39, 33.81, 33.59, 32.36, 32.18, 31.61, 31.38, 30.91, 30.00, 27.31, 26.03, 25.69, 19.73, 18.68.

Scheme 6: Synthesis of chemiluminescence probe 2

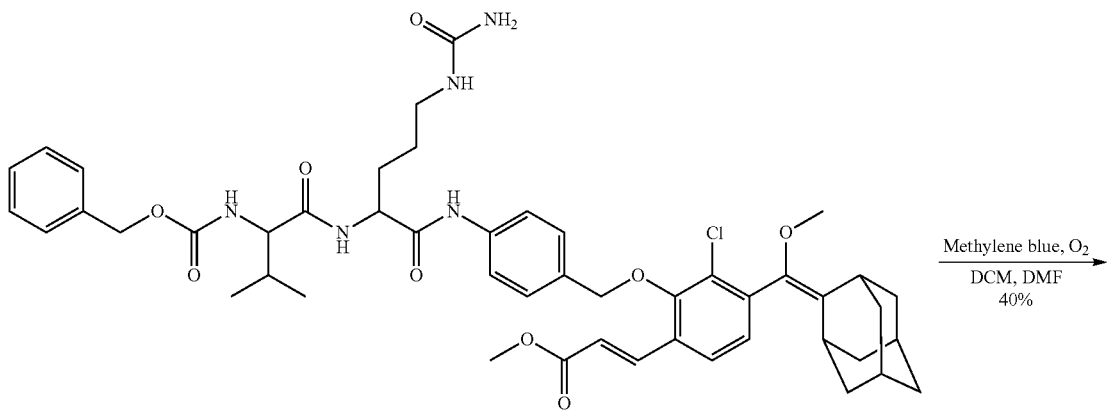

2b

-continued

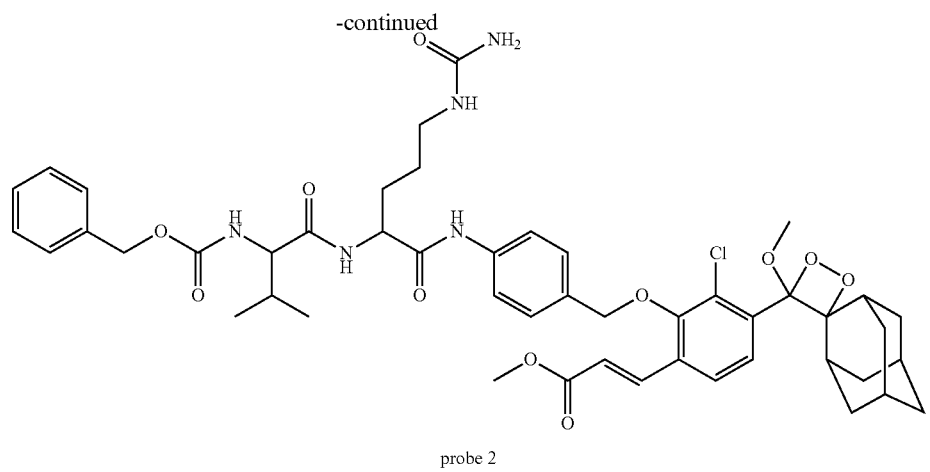

probe 2

Synthesis of Z-Val-Cit-PABA-7HC

As depicted in Scheme 7, compound 1b (40 mg, 0.064 mmol, 1 eq) and 7-hydroxycoumarin (12 mg, 0.07 mmol, 1.1 eq) were dissolved in 0.5 mL DMF and $K_2CO_3$ (20 mg, 0.141 mmol, 2.2 eq) was added. The reaction was monitored by TLC (MeOH:DCM 10:90). After completion, the reaction mixture diluted with EtOAc and was washed with saturated $NH_4Cl$. The organic layer was separated, washed with brine, dried over $Na_2SO_4$, filtered and the solvent was evaporated under reduced pressure. The crude product was purified by column chromatography on silica gel (MeOH:DCM 10:90) to afford the Z-Val-Cit-PABA-7HC (29 mg, 71% yield) as a yellowish solid. MS (ES+): m/z calc. for $C_{35}H_{39}N_5O_8$: 657.28; found: 680.52 $[M+Na]^+$.

Scheme 7: Synthesis of Z-Val-Cit-PABA-7HC

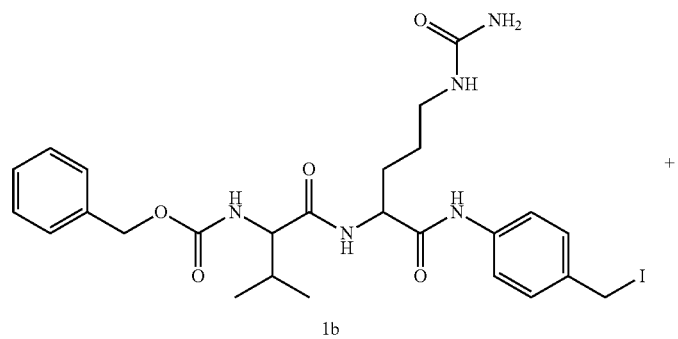

1b

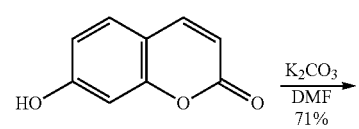

-continued

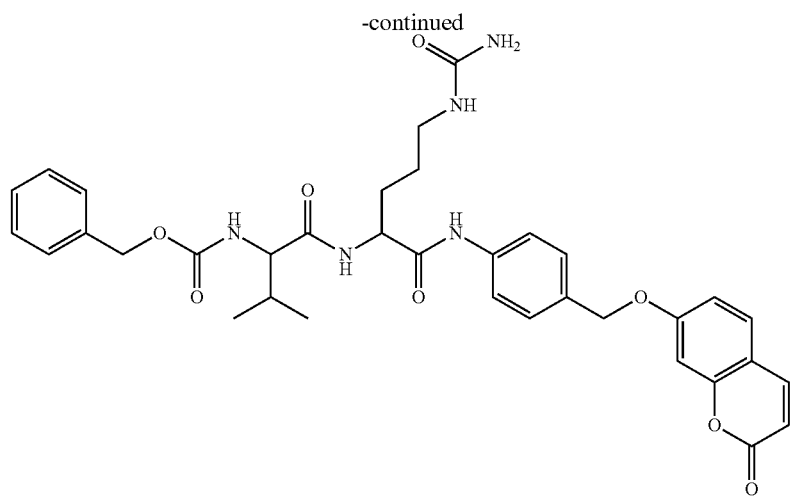

Synthesis of Probe 3

Compound 3b. As depicted in Scheme 8, compound 3a (Dubowchik et al., 2002) (100 mg, 0.2 mmol, 1 eq) was dissolved in 7 mL of ACN and cooled to 0° C. Sodium iodide (90 mg, 0.6 mmol, 3 eq) was added followed by the rapid addition of TMS-Cl (78 µl, 0.6 mmol, 3 eq). The reaction was allowed to warm up to room temperature and monitored by TLC (MeOH:DCM 10:90). Upon completion, the reaction mixture was diluted with EtOAc, and washed with saturated $Na_2S_2O_3$ followed by brine. The organic layer was separated, dried over $Na_2SO_4$, filtered and the solvent was evaporated under reduced pressure, to afford compound 3b (108 mg, 76% yield) as a yellowish solid. MS (ES+): m/z calc. for $C_{33}H_{38}IN_5O_5$: 711.19; found: 712.5 [M+H]$^+$. $^1$H NMR (400 MHz, DMSO) δ 10.10 (d, J=7.4 Hz, 1H), 8.13 (d, J=7.1 Hz, 1H), 7.87 (d, J=7.4 Hz, 2H), 7.73 (t, J=7.4 Hz, 2H), 7.59 (d, J=8.2 Hz, 1H), 7.52 (d, J=8.2 Hz, 2H), 7.46-7.25 (m, 4H), 7.21 (s, 1H), 4.70 (s, 1H), 4.60 (s, 1H), 4.41 (s, 2H), 4.34-4.15 (m, 4H), 3.94-3.89 (m, 2H), 3.00 (s, 1H), 2.94 (s, 1H), 1.97 (d, J=6.4 Hz, 1H), 1.67 (s, 1H), 1.59 (s, 1H), 1.50-1.26 (m, 2H), 1.21 (s, 1H), 0.86 (d, J=6.8 Hz, 3H), 0.84 (d, J=6.7 Hz, 3H). $^{13}$C NMR (101 MHz, DMSO) δ 171.84, 171.23, 159.46, 156.65, 144.43, 144.30, 141.23, 139.50, 132.96, 130.06, 128.18, 127.61, 125.90, 120.64, 120.11, 119.64, 118.09, 66.20, 63.11, 60.57, 57.25, 53.64, 47.21, 46.71, 39.83, 39.63, 39.42, 30.97, 29.93, 29.53, 27.29, 19.75, 18.82.

Scheme 8: Synthesis of compound 3b

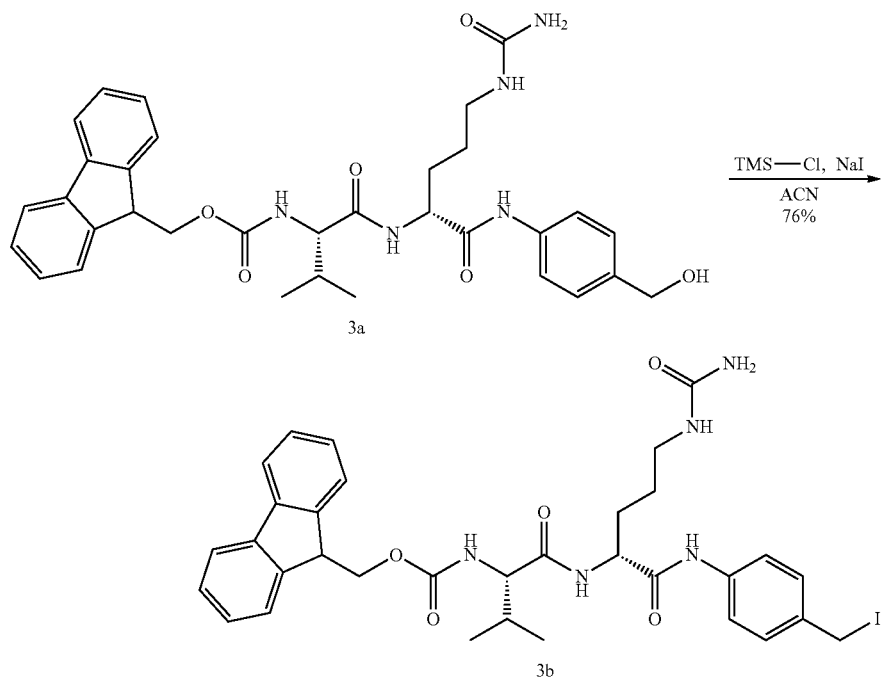

Compound 3c. As depicted in Scheme 9, compound 2a (120 mg, 0.31 mmol, 1.2 eq) was dissolved in dry DMF, under argon atmosphere and cooled to 0° C. Sodium iodide (11.2 mg, 0.28, 1.1 eq) was added, and the reaction was allowed to warm to room temperature. After stirring for 15 minutes, compound 3b (184 mg, 0.26 mmol, 1 eq) was added and the reaction was monitored by TLC (MeOH: DCM 10:90). Upon completion, the solvent was removed under reduced pressure. The resulting oil was precipitated with 2 mL of EtOAc, followed by trituration with Et$_2$O (7 mL) for 10 minutes. The mixture was then filtered via vacuum filtration and the solid dried to provide compound 3c (236 mg, 68%) as an off-white solid. MS (ES+): m/z calc. for C$_{55}$H$_{62}$ClN$_5$O$_9$: 971.42; found: 972.7 [M+H]$^+$. $^1$H NMR (400 MHz, DMSO) δ 10.10 (s, 1H), 8.13 (d, J=7.4 Hz, 1H), 7.87 (d, J=7.5 Hz, 2H), 7.77 (dd, J=8.3, 4.4 Hz, 2H), 7.72 (d, J=7.8 Hz, 2H), 7.60 (d, J=8.3 Hz, 2H), 7.41 (dd, J=17.4, 8.5 Hz, 3H), 7.31 (t, J=7.9 Hz, 4H), 7.09 (d, J=8.0 Hz, 1H), 6.64 (d, J=16.2 Hz, 1H), 5.98-5.95 (m, 1H), 5.40 (s, 2H), 4.92 (dd, J=15.0 Hz, 2H), 4.41 (s, 1H), 4.31-4.18 (m, 3H), 3.96-3.86 (m, 1H), 3.70 (s, 3H), 3.36 (dd, J=14.0, 7.0 Hz, 1H), 3.20 (s, 3H), 3.17 (s, 1H), 3.07-2.97 (m, 1H), 2.97-2.86 (m, 1H), 2.03-1.82 (m, 6H), 1.80-1.50 (m, 9H), 1.50-1.27 (m, 2H), 1.07 (t, J=7.0 Hz, 1H), 0.87 (d, J=6.7 Hz, 3H), 0.84 (d, J=6.7 Hz, 3H). $^{13}$C NMR (101 MHz, DMSO) δ 171.82, 171.21, 166.95, 159.41, 156.64, 153.54, 144.44, 144.31, 141.23, 139.86, 138.41, 137.90, 130.92, 130.75, 130.10, 129.87, 129.26, 128.17, 127.60, 126.39, 125.91, 120.63, 119.33, 76.03, 66.21, 65.46, 60.57, 57.06, 53.63, 52.16, 47.21, 38.95, 38.63, 36.98, 32.93, 30.99, 30.00, 29.55, 28.09, 27.34, 19.75, 18.80, 15.70.

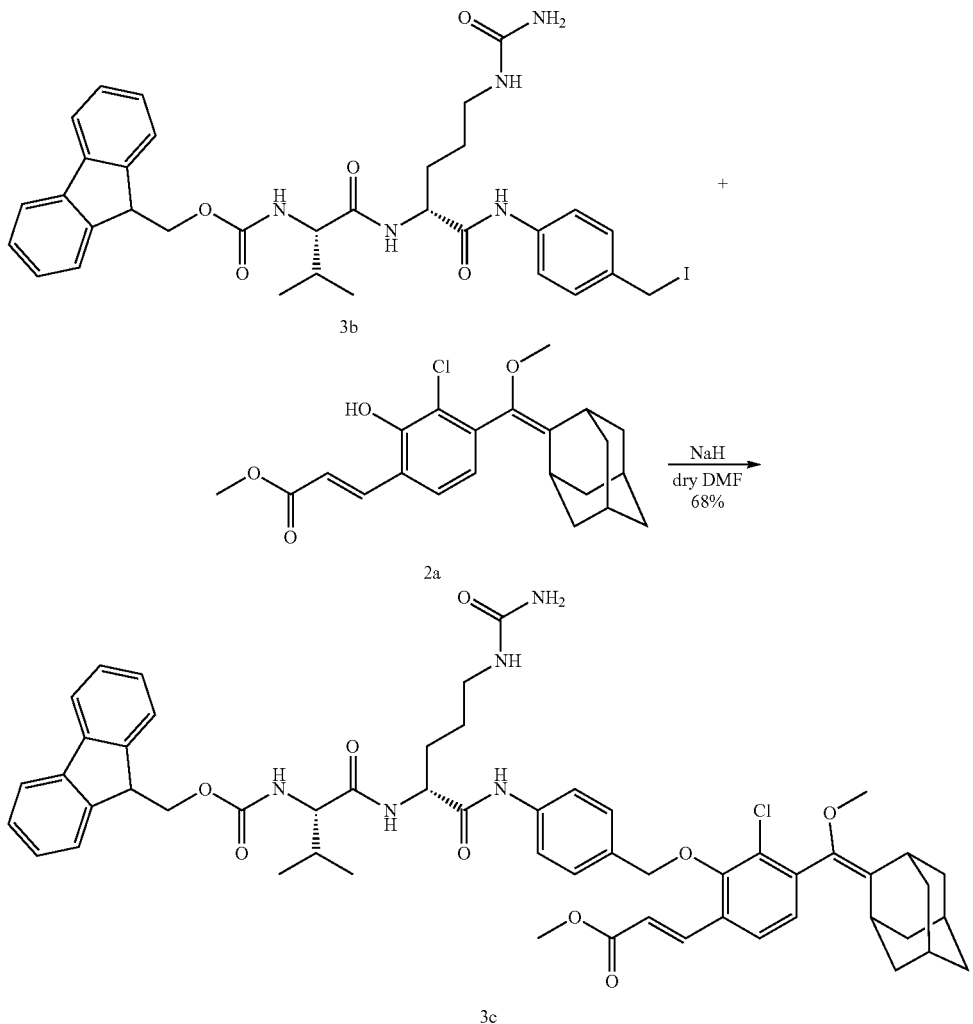

Scheme 9: Synthesis of compound 3c

Compound 3d. As depicted in Scheme 10, compound 3c (220 mg, 0.23 mmol, 1 eq) was dissolved in DMF (6 mL) and diethylamine (2 mL) was added. The reaction was monitored by RP-HPLC (50-100% ACN in water, 20 min). Upon completion, the solvent was removed under reduced pressure. The resulting oil was precipitated with 1.5 mL of EtOAc, followed by trituration with Et$_2$O (20 mL) for 10 minutes. The mixture was then filtered via vacuum filtration and the solid dried to provide compound 3d (140 mg, 82%) as an off-white solid. MS (ES+): m/z calc. for C$_{40}$H$_{52}$ClN$_5$O$_7$: 749.36; found: 750.6 [M+H]$^+$. $^1$H NMR (400 MHz, DMSO) δ 10.18 (s, 1H), 8.23 (s, 1H), 7.81-7.71 (m, J=11.2 Hz, 2H), 7.60 (d, J=8.3 Hz, 2H), 7.33 (d, J=8.3 Hz, 2H), 7.10 (d, J=8.1 Hz, 1H), 6.63 (d, J=16.1 Hz, 1H), 5.98 (s, 1H), 5.42 (s, 2H), 4.93 (dd, J=30.5, 9.9 Hz, 2H), 4.47

(s, 1H), 3.71 (s, 3H), 3.20 (s, 3H), 3.17 (s, 1H), 3.13 (d, J=4.7 Hz, 1H), 3.05-2.97 (m, 1H), 2.97-2.88 (m, 1H), 1.94-1.85 (m, J=24.5 Hz, 6H), 1.78-1.55 (m, 9H), 1.46-1.32 (m, 3H), 1.22 (s, 2H), 0.88 (d, J=6.7 Hz, 3H), 0.80 (d, J=6.7 Hz, 3H). $^{13}$C NMR (101 MHz, DMSO) δ 173.82, 171.24, 166.96, 159.43, 153.55, 139.87, 139.72, 138.42, 137.91, 131.01, 130.77, 130.11, 129.88, 129.26, 128.19, 126.40, 120.58, 119.41, 76.02, 59.72, 57.06, 53.17, 52.16, 40.04, 39.83, 39.62, 39.41, 38.96, 38.63, 36.98, 32.92, 31.62, 30.46, 29.55, 28.08, 27.26, 22.60, 19.85, 17.61, 14.50.

CDCl$_3$) δ 155.54, 152.49, 145.38, 125.32, 121.86, 71.92, 70.69, 70.55, 68.62, 68.33, 59.02.

Scheme 11: Synthesis of compound 3e

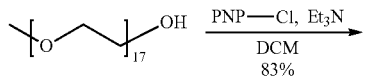

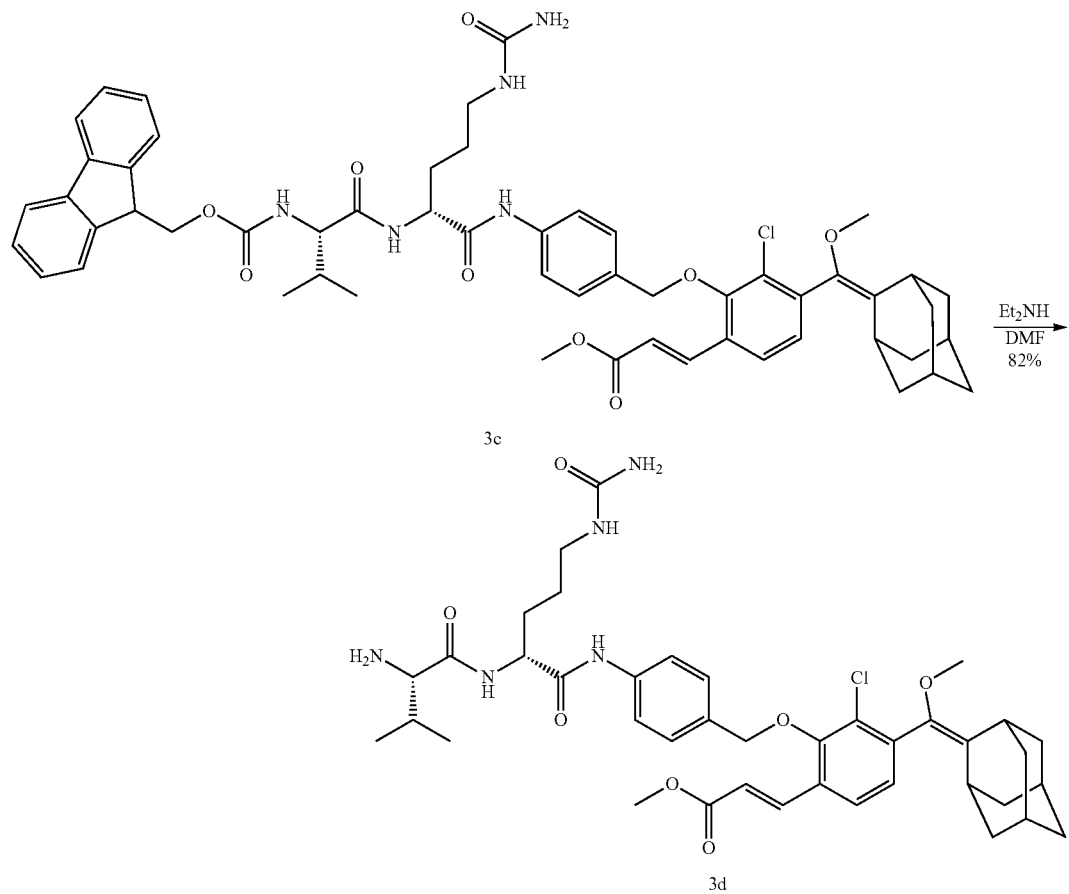

Compound 3e. As depicted in Scheme 11, mPEG$_{780}$ (100 mg, 0.128 mmol, 1 eq) was dissolved in dry DCM, under argon atmosphere, and cooled to 0° C. Et$_3$N (36 μl, 0.256 mmol, 2 eq) and p-nitrophenyl chloroformate (PNP-Cl, 52 mg, 0.256 mmol, 2 eq) were added and the reaction was allowed to warm up to room temperature. The reaction was monitored by TLC (MeOH:DCM 10:90). Upon completion, the reaction mixture was diluted with DCM, and washed with saturated NH$_4$Cl. The organic layer was separated, dried over Na$_2$SO$_4$, filtered and the solvent was evaporated under reduced pressure. The crude product was purified by column chromatography on silica gel (MeOH:DCM 20:80) to afford compound 3e (101 mg, 83% yield) as a white-yellowish solid. MS (ES+): m/z calc. for C$_{42}$H$_{75}$NO$_{22}$: 946.04; found: 946.8. $^1$H NMR (400 MHz, CDCl3) δ 8.2 (d, 2H, J=8 Hz), 7.32 (d, 2H, J=8 Hz), 4.41-4.33 (m, 2H), 3.77-3.72 (m, 2H), 3.64-3.60 (m, 6H), 3.56-3.58 (m, 56H), 3.46-3.48 (m, 2H), 3.30 (s, 3H). $^{13}$C NMR (101 MHz, Probe 3. As depicted in Scheme 12, compound 3d (10 mg, 0.013 mmol, 1 eq) and compound 3e (19 mg, 0.02 mmol, 1.5 eq) were dissolved in DMF and a few drops of Et$_3$N were added. The reaction was heated to 50° C. overnight. The reaction was monitored by RP-HPLC (30-100% ACN in water, 20 min). Upon completion, the reaction mixture was concentrated by evaporation under reduced pressure and the crude product was used for the next step without further purification. MS (ES+): m/z calc. for C$_{76}$H$_{122}$ClN$_5$O$_{26}$: 1557.25; found: 790.4 [(M+Na)/2]$^+$.

Scheme 12: Synthesis of chemiluminescence probe 3

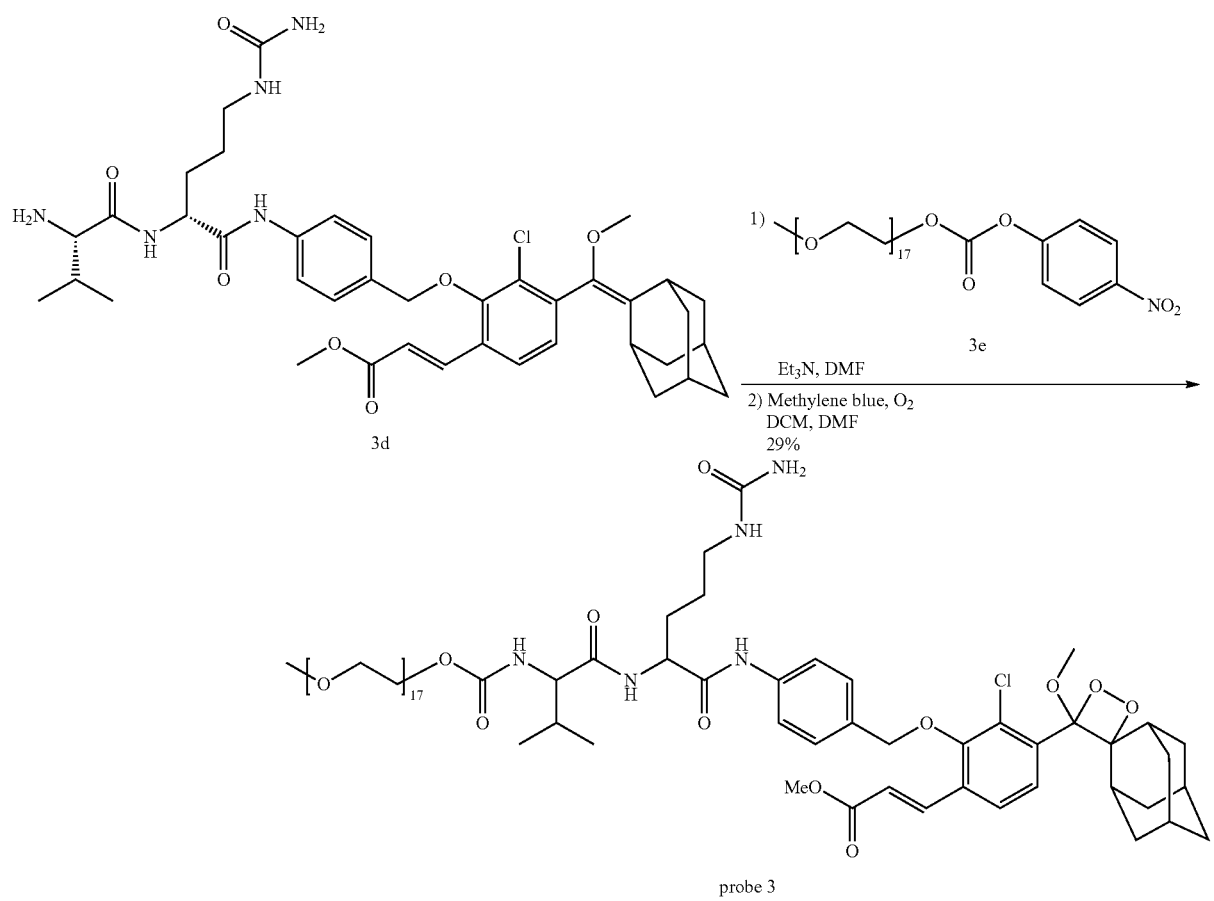

probe 3

The crude (12 mg, 0.008 mmol) was dissolved in 5 mL DCM. A few milligrams of methylene blue were added and oxygen was bubbled through the solution, while irradiating with yellow light. The reaction was monitored by RP-HPLC (30-100% ACN in water, 20 min). Upon completion, the reaction mixture was concentrated by evaporation under reduced pressure and the crude product was purified by preparative RP-HPLC (30-100% ACN in water, 20 min) to afford probe 3 (6 mg, 29% yield, over two steps) as a white solid. MS (ES+): m/z calc. for $C_{76}H_{122}ClN_5O_{28}$: 1587.80; found: 1589.0 [M+H]$^+$. $^1$H NMR (400 MHz, DMSO) δ 10.06 (s, 1H), 8.05 (d, J=7.6 Hz, 1H), 7.94 (d, J=8.4 Hz, 1H), 7.77 (d, J=8.4 Hz, 1H), 7.74-7.68 (m, 1H), 7.60 (d, J=8.6 Hz, 2H), 7.32 (d, J=8.3 Hz, 2H), 7.23 (d, J=8.7 Hz, 1H), 6.67 (d, J=16.1 Hz, 2H), 5.95 (t, J=5.5 Hz, 1H), 5.39 (s, 2H), 4.88 (t, J=11.6 Hz, 2H), 4.41 (d, J=5.1 Hz, 2H), 4.05 (s, 2H), 3.88 (d, J=11.7 Hz, 2H), 3.71 (s, 3H), 3.70 (s, 1H), 3.56 (d, J=4.5 Hz, 6H), 3.49 (s, 56H), 3.41 (dd, J=5.8, 3.5 Hz, 2H), 3.22 (s, 3H), 3.11 (s, 3H), 3.07-2.90 (m, 2H), 2.87 (s, 1H), 2.28-2.11 (m, 2H), 2.01-1.83 (m, 3H), 1.64 (dd, J=48.9, 13.1 Hz, 9H), 1.39 (dd, J=52.0, 12.3 Hz, 5H), 1.22 (s, 2H), 0.86 (d, J=6.7 Hz, 3H), 0.82 (d, J=6.7 Hz, 3H). $^{13}$C NMR (101 MHz, DMSO) δ 171.80, 171.24, 169.86, 169.80, 168.91, 166.76, 164.34, 159.45, 156.78, 154.29, 152.20, 139.94, 137.90, 134.91, 133.96, 133.65, 131.83, 131.41, 130.85, 130.20, 129.00, 127.38, 126.60, 123.76, 121.77, 119.46, 116.80, 111.80, 111.77, 96.06, 76.18, 71.86, 70.36, 70.16, 69.39, 64.06, 60.53, 58.62, 53.54, 53.29, 52.27, 49.94, 40.74, 40.54, 40.33, 40.12, 39.91, 39.70, 39.49, 36.46, 36.40, 33.88, 33.78, 33.65, 32.42, 32.23, 31.77, 31.44, 30.94, 30.07, 29.57, 29.21, 27.34, 26.08, 25.79, 22.66, 19.77, 18.70.

Synthesis of Probe 4

Compound 4b. As depicted in Scheme 13, compound 3d (10 mg, 0.013 mmol, 1 eq) and compound 4a (Ikeda et al., 2012) were dissolved in DMF (0.5 mL) and a few drops of Et$_3$N were added. The Reaction was monitored by RP-HPLC (30-100% ACN in water, 20 min). Upon completion, the reaction mixture concentrated under reduced pressure. The crude product was further reacted without purification. The crude product and few milligrams of methylene blue were dissolved in 5 mL of DCM and a few drops of DMF (to enhance solubility). Oxygen was bubbled through the solution while irradiating with yellow light. The reaction was monitored by RP-HPLC (30-100% ACN in water, 20 min). Upon completion, the reaction mixture was concentrated by evaporation under reduced pressure. The crude product was purified by preparative RP-HPLC (30-100% ACN in water, 20 min) to afford compound 4b (11 mg, 76% yield) as a white solid. MS (ES+): m/z calc. for $C_{50}H_{63}ClN_6O_{12}$: 974.42; found: 975.8 [M+H]$^+$. $^1$H NMR (400 MHz, DMSO) δ 10.02 (s, 1H), 8.09 (d, J=7.5 Hz, 1H), 7.94 (d, J=8.4 Hz, 1H), 7.78 (t, J=9.4 Hz, 2H), 7.70 (d, J=16.2 Hz, 1H), 7.60 (d, J=8.5 Hz, 2H), 7.32 (d, J=7.2 Hz, 2H), 6.98 (s, 2H), 6.67 (d, J=16.2 Hz, 1H), 5.97 (s, 1H), 5.40 (s, 2H), 4.95-4.80 (m, 2H), 4.37 (d, J=5.4 Hz, 1H), 4.26-4.10 (m, 1H), 3.71 (s, 3H), 3.35 (t, J=7.0 Hz, 3H), 3.10 (s, 3H), 3.06-2.97 (m, 1H), 2.97-2.89 (m, 1H), 2.87 (s, 1H), 2.29-2.02 (m, 3H), 1.99-1.85 (m, 2H), 1.79-1.52 (m, 9H), 1.47 (dd, J=14.3, 7.9 Hz, 6H), 1.32 (d, J=11.3 Hz, 2H), 1.18 (dd, J=17.9, 10.0 Hz, 3H), 0.84 (d, J=6.7 Hz, 3H), 0.80 (d, J=6.7 Hz, 3H). $^{13}$C NMR (101 MHz, DMSO) δ 172.80, 171.61, 171.22, 166.74, 159.43, 154.25, 139.89, 137.90, 134.99, 130.19, 127.40, 121.79, 119.37, 111.72, 95.96, 76.27, 58.07, 53.63, 52.24, 49.96, 39.83, 39.62, 39.42, 37.54, 36.39, 35.45, 33.58, 32.18, 31.38, 30.93, 29.82, 28.30, 27.36, 26.31, 26.02, 25.69, 25.44, 19.78, 18.72.

mmol, 1.1 eq) were dissolved in DMF and a few drops of Et$_3$N were added. The reaction was monitored by RP-HPLC (30-100% ACN in water, 20 min). Upon completion, the reaction mixture was concentrated by evaporation under reduced pressure. The crude product was purified by preparative RP-HPLC (30-100% ACN in water, 20 min) to afford probe 4 (8 mg, 68% yield) as a white solid. MS (ES+): m/z calc. for $C_{73}H_{109}ClN_{16}O_{18}S$: 1566.26; found: 784.1 [(M+H)/2]$^+$. $^1$H NMR (400 MHz, DMSO) δ 10.06 (s, 1H), 8.88-8.74 (m, 1H), 8.36 (s, 2H), 8.23-8.06 (m, 4H), 7.93 (t, J=12.1 Hz, 1H), 7.85-7.74 (m, 9H), 7.71 (d, J=16.2 Hz, 1H), 7.60 (t, J=7.5 Hz, 2H), 7.33 (d, J=8.4 Hz, 3H), 6.70-6.65 (m, 1H), 6.05 (s, 1H), 4.93-4.83 (m, 2H), 4.46-4.02 (m, 13H),

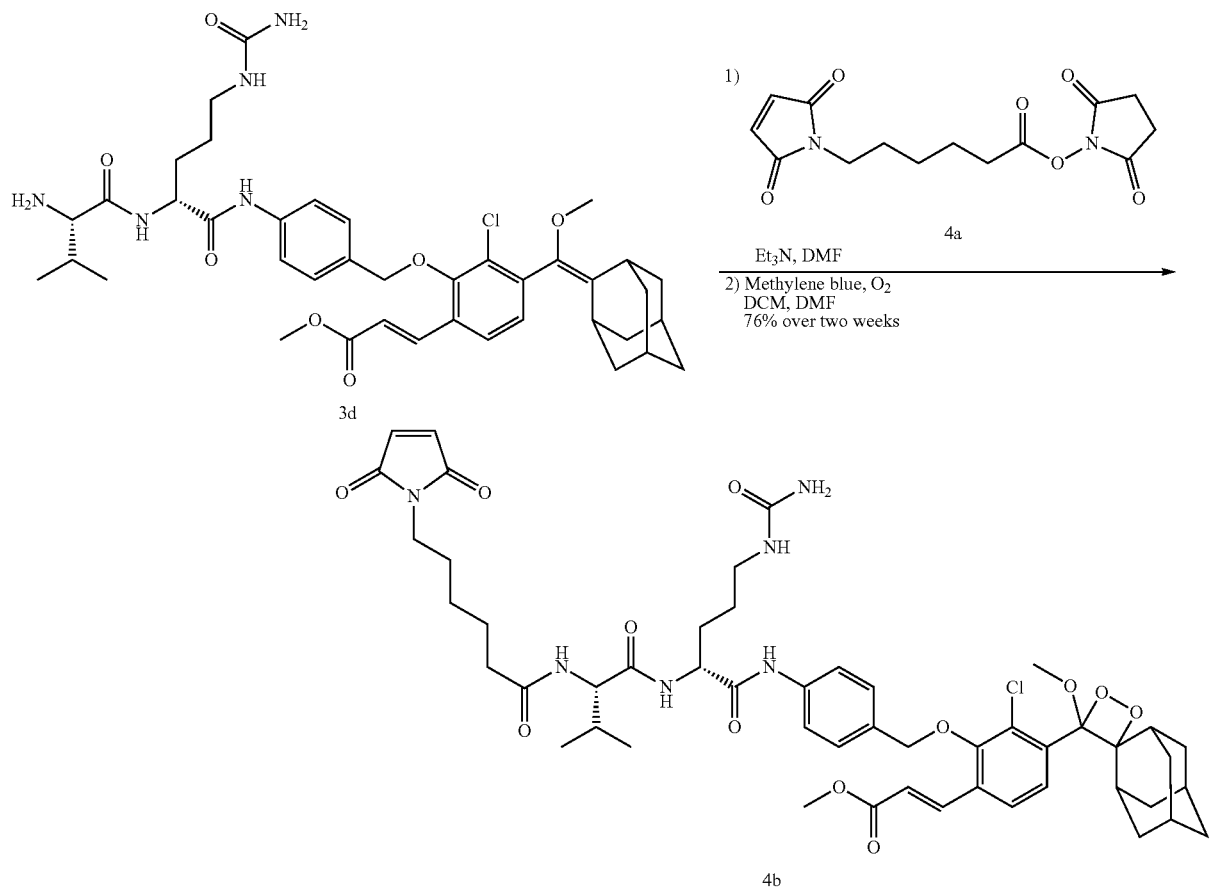

Scheme 13: Synthesis of compound 4b

CGKRK. Peptide CGKRK (Cys-Gly-Lys-Arg-Lys) was synthesized via Fmoc-Solid Phase Peptide Synthesis. Fmoc-Lys(Boc)-Wang resin was swirled in DMF for 30 min. Fmoc deprotection was done with 20% piperidine (15 minutes) followed by coupling of the next amino acid (4 eq) with HBTU (4 eq) in a mixture of DIPEA (6 eq) and DMF (30 minutes). These two steps were repeated until the sequence is completed. Finally, Fmoc deprotection of the cysteine was completed and the CGKRK sequence was cleaved from the resin using TFA/TIPS/H$_2$O (90/5/5) solution. The peptide was precipitated and washed with cold diethyl ether solution and lyophilized. The product was afforded as a white precipitate. MS (ES+): m/z calc. for $C_{23}H_{46}N_{10}O_6S$: 590.33; found: 591.3 [M+H]$^+$.

Probe 4. As depicted in Scheme 14, compound 4b (7 mg, 0.007 mmol, 1 eq) and CGKRK peptide (7.5 mg, 0.008

3.85 (s, 2H), 3.71 (s, 3H), 3.33 (dd, J=14.4, 7.3 Hz, 2H), 3.24-2.90 (m, 8H), 2.87 (s, 1H), 2.71 (dd, J=13.8, 9.6 Hz, 4H), 2.52 (d, J=3.0 Hz, 1H), 2.28-2.04 (m, 2H), 2.01-1.86 (m, 1H), 1.76-1.40 (m, 28H), 1.37-1.26 (m, 6H), 1.23-1.11 (m, 3H), 0.85 (d, J=6.7 Hz, 3H), 0.81 (d, J=6.8 Hz, 3H). $^{13}$C NMR (101 MHz, DMSO) δ 177.35, 175.41, 173.84, 172.76, 171.95, 171.85, 171.23, 168.35, 167.82, 166.74, 159.53, 159.12, 158.80, 157.34, 154.24, 139.88, 137.89, 134.85, 131.77, 130.72, 130.19, 128.87, 127.39, 126.57, 121.77, 119.37, 118.78, 115.83, 111.71, 95.95, 76.26, 57.99, 53.63, 52.67, 52.55, 52.24, 49.95, 42.52, 40.02, 39.81, 39.61, 39.40, 39.21, 39.09, 38.71, 36.39, 35.45, 33.81, 33.59, 32.19, 31.60, 31.38, 30.99, 30.88, 29.84, 27.35, 27.11, 26.36, 26.02, 25.69, 25.45, 22.85, 22.76, 19.78, 18.70.

Scheme 14: Synthesis of chemiluminescence probe 4

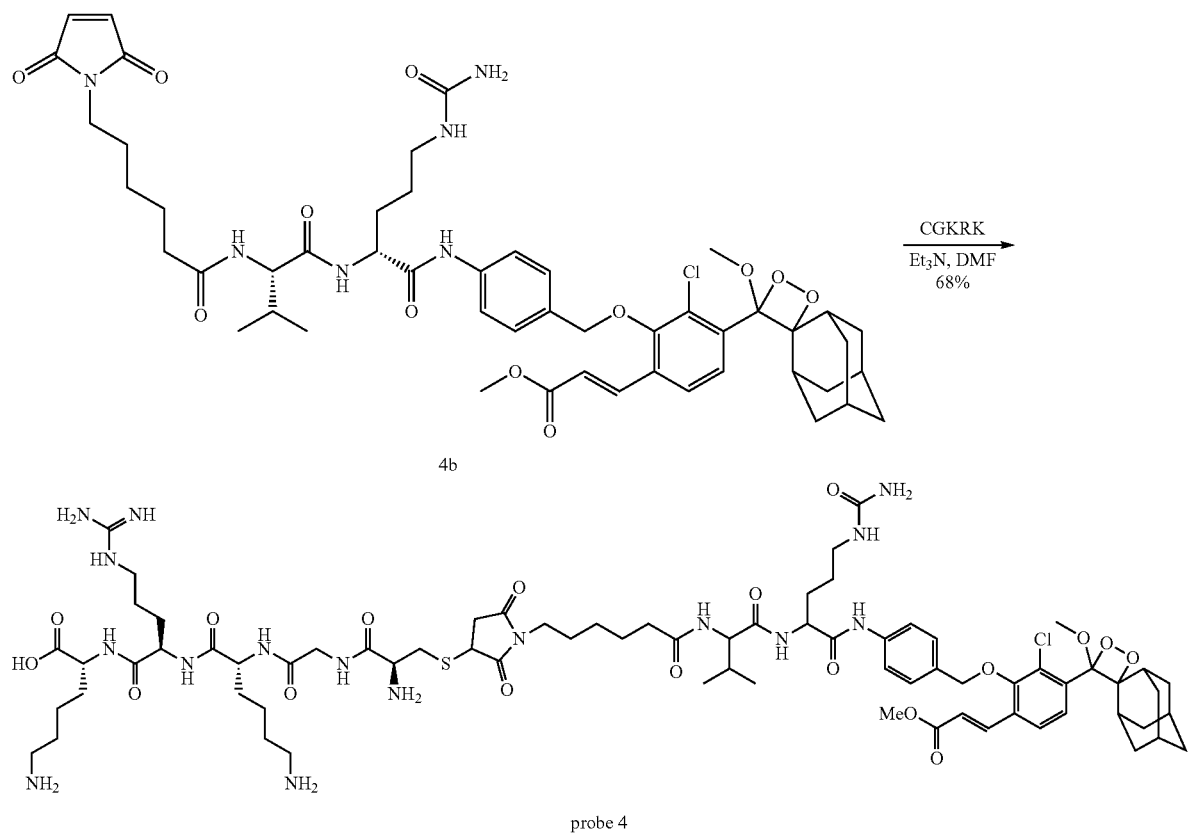

Spectroscopic Data

The activity buffer contained: phosphate buffer 0.1M, 55 mM NaCl, 1 mM EDTA, 5 mM glutathione. All spectroscopic measurements were conducted in triplicates. The blank measurements for limit of detection calculation were repeated ten times. Limit of detection (LOD) was calculated as such:

$$LOD = \text{Mean}_{blank} + 3 \times SD$$

wherein SD—standard deviation.

Chemiluminescence Microscopy Imaging

Chemiluminescence images were acquired using Olympus LV200 inverted microscope fitted with an EMCCD camera (Hamamatsu $C_{9100}$-13). RAW 264.7 Abelson murine leukemia virus-induced tumor cells, CT26CL25 colon carcinoma cells and NIH 3T3 mouse fibroblast (control) cells were grown on 35mm glass bottom petri dishes at 37° C. for 24 h. Cell culture medium was changed to Molecular Probes® Live Cell Imaging Solution containing 5 μM of probes MR 3-128 or MR 3-131. Cells were incubated for another 20 minutes at 37° C. For visualization of chemiluminescence emission, images were recorded with 20 minutes exposure times.

Images were imported in ImageJ software. For image visualization a rolling ball filter (with 20 pixel radius) was applied and image brightness and contrast were adjusted.

Study 1. Probes 2-4 are Effective in Detection of Cathepsin B

In this Study, four probes identified herein as probes 1, 2, 3 and 4 were synthesized as described in the Experimental. Probe 1 was based on the conventional Schaap adamantylidene-dioxetane, with cathepsin B labile protecting group, while probe 2 was constructed with the addition of an elongated pi-system and an electron-withdrawing group. This donor-acceptor pair design increases the emission of the luminophore under physiological conditions, allowing it to serve as a good luminophore for one-step assays with enzymatic activation, and live-cell imaging. To improve the solubility in water and the odds of the probes entering cells, we also synthesized probes 3 and 4. In probe 3, the N-carboxybenzyl (Cbz) addendum was replaced by a medium-length PEG. PEG is vastly utilized in the construct of biologically applicable systems, as it is water soluble, improves the pharmacokinetic properties of attached molecules and FDA approved.

In probe 4, a linker was added and attached to CGKRK (Cys-Gly-Lys-Arg-Lys) peptide. The CGKRK peptide contains multiple basic residues. A high content of basic residues is a shared characteristic among internalizing peptides, making the CGKRK an effective cell-penetrating and solubilizing peptide. The penta-peptide was first identified in a screening with transgenic mouse epidermal cancers. When a small molecule is coupled to the CGKRK peptide, it internalizes the conjugate into most target tumor cells but does not uptake in normal tissues. This is due to the overexpression of p32 receptor, which recognizes CGKRK, on the surface of activated endothelial and tumor cells. As CGKRK is recognized by multiple types of cancers, which mostly correlate to the cancers in which cathepsin B is overexpressed, we hoped to see an increase of cell-uptake in live cancerous cells when using probe 4.

Figure 1B:
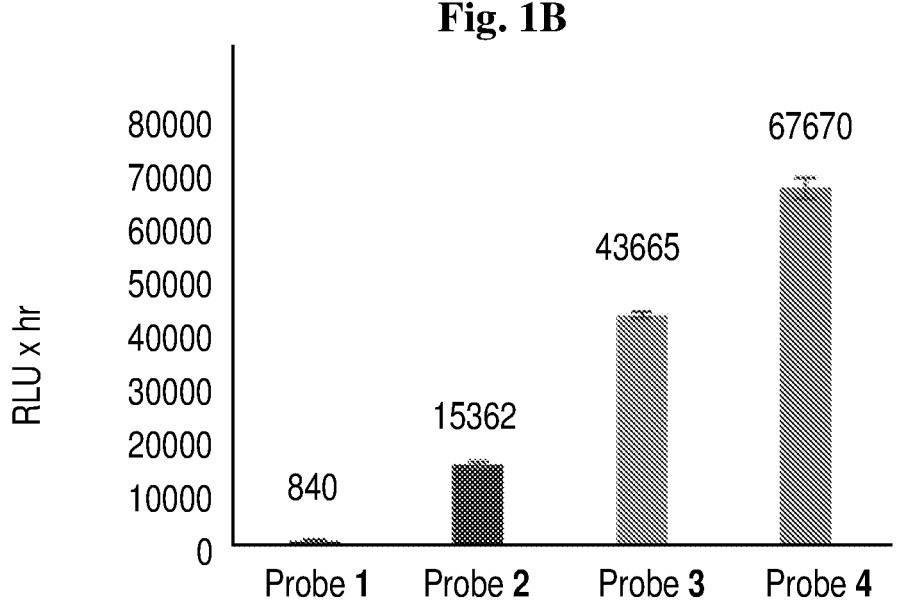
Figure 1C:
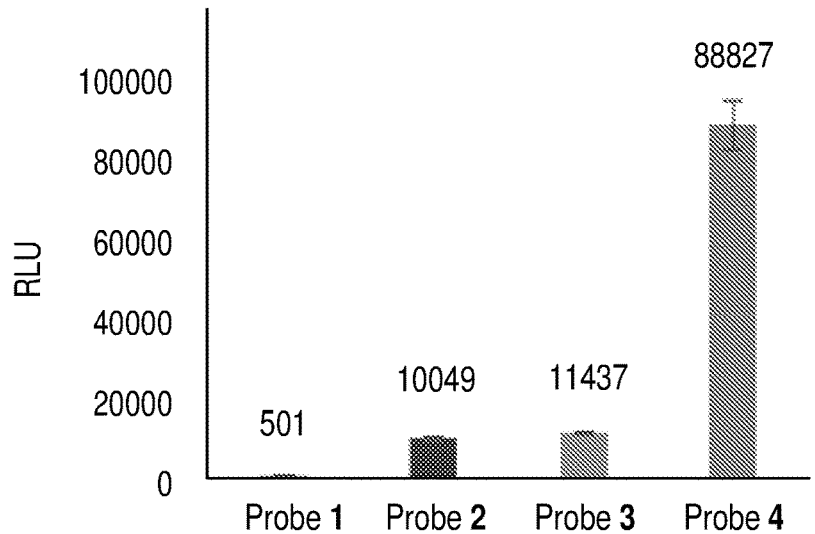
Figure 2:
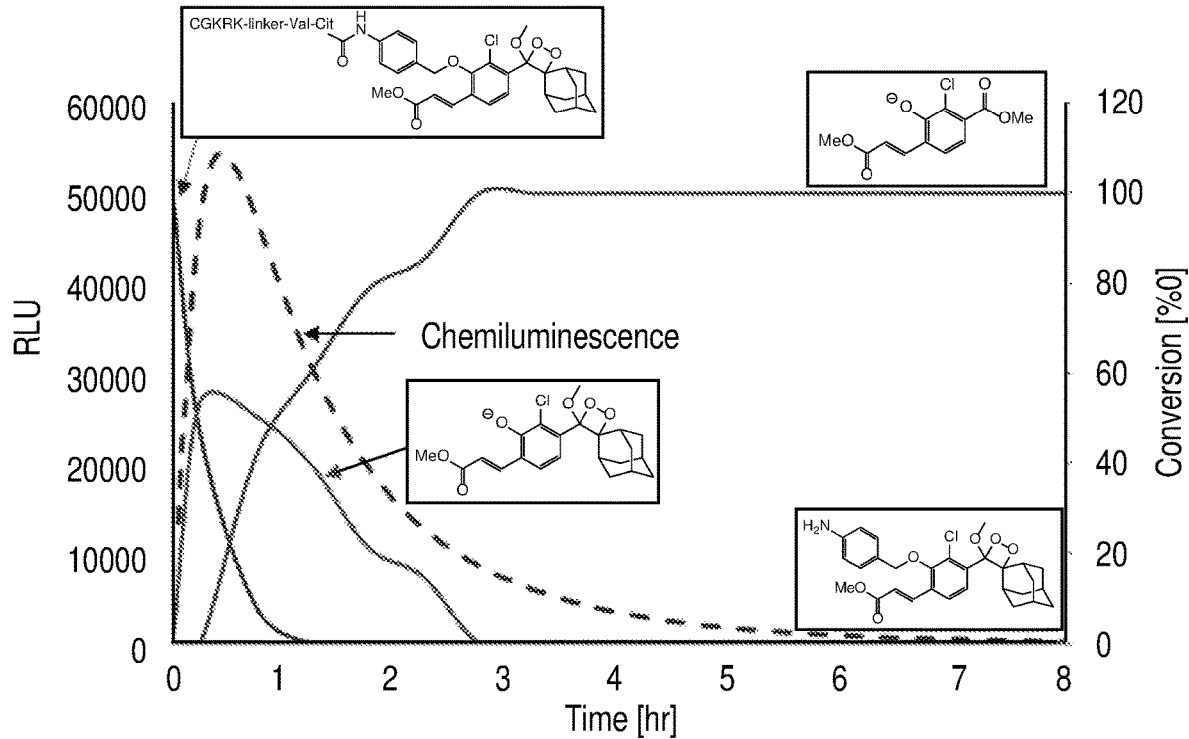
FIG. 2 shows the chemiluminescence kinetic profile and HPLC analysis of the enzymatic degradation of probe 4 [10 µM] in activity buffer (pH 7.4, 10% DMSO) with 2.5 U/mL cathepsin B. Probe 4 is shown schematically.

Next, chemiluminescence emission of the probes, as a function of time was measured, with or without the addition of cathepsin B. The kinetic profiles of the chemiluminescence signals and their relative total-photon emissions are shown in FIGS. 1A and 1B, respectively. The probes exhibit a characteristic chemiluminescence kinetic profile upon the addition of cathepsin B, with an initial signal rise to a maximum followed by a slower decrease until termination. There is a distinct increase in the chemiluminescent signal from probe 1 onto probes 2, 3 and 4. Probe 1 produced extremely weak emission (FIG. 1A, inset), as expected due to its lack of the added donor-acceptor pair. From then on, a pattern of increased chemiluminescent signal is seen, correlating to the addendum change and the improved probe solubility in aqueous media. Evaluating the probes for forthcoming cell imaging required us to also assess the maximal signal yielded by each probe, as it will culminate in higher sensitivity and resolution (FIG. 1C). The maximal signal of the different probes pales in comparison to that of probe 4, making it the leading choice for further investigation. No light emission was observed from the probes in the absence of cathepsin B.

To confirm the connection between the enzymatic degradation and chemiluminescent signal of the probes, HPLC was used to follow the enzymatic degradation of probe 4. HPLC analysis reveals the rapid enzymatic disassembly of probe 4 and the ultra-fast 1,6-elimination of the aniline linker. Comparisons of the HPLC and chemiluminescence data show strong correlation between the chemiluminescence maximal signal, and the termination of the enzymatic cleavage. Moreover, a relationship between the chemiluminescence decay and the chemiexcitation process is apparent (as seen by the kinetic degradation of the unmasked phenolate to the benzoate). Furthermore, this demonstrates the efficiency and swiftness of the decay of the benzoate ester to its ground state (which is accompanied by the emission of light).

Figure 3:
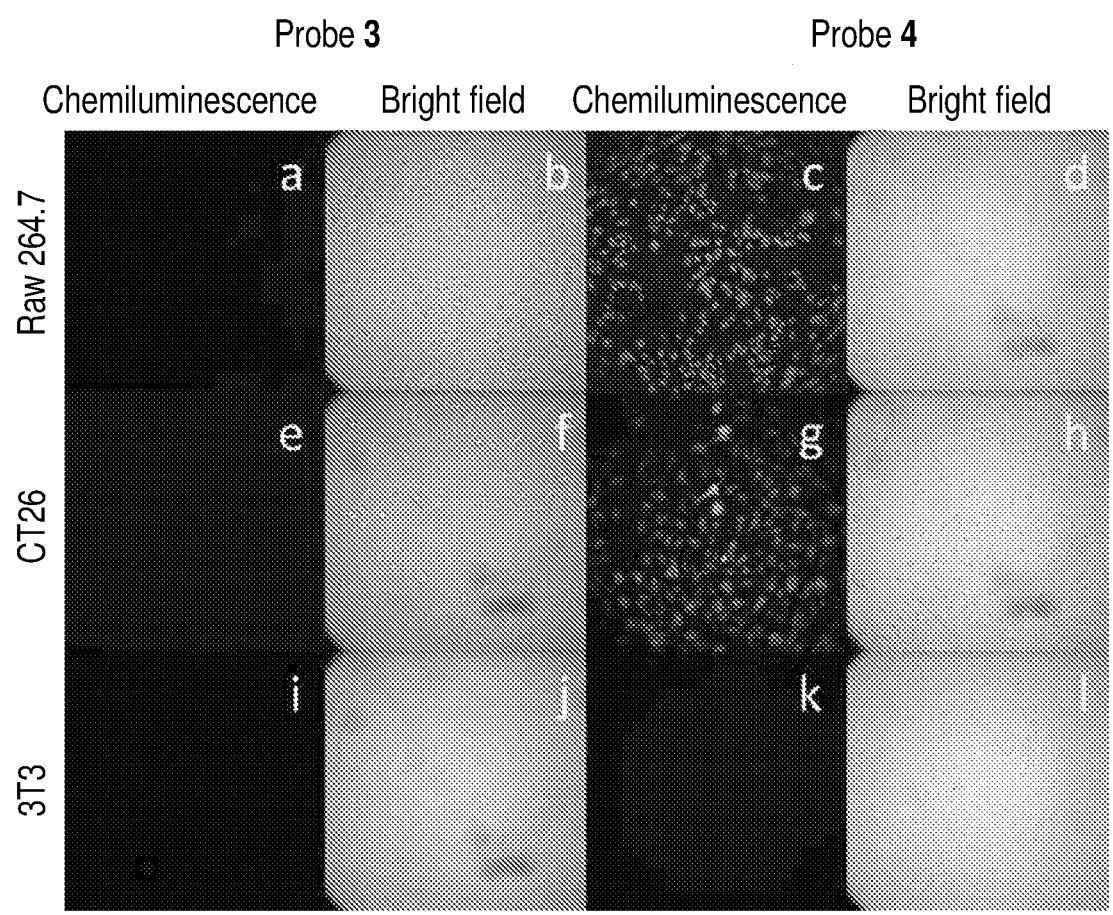
FIG. 3 shows the transmitted light and chemiluminescence imaging of cathepsin B activity in Raw 264.7, CT26 tumor cells, and 3T3 normal cells. Images were obtained following 30 min incubation with cell culture medium containing either probe 3 or probe 4 (5 µM), and were taken using the LV200 Olympus microscope using a 60× objective and 20 min exposure time. Chemiluminescence microscopy image and transmitted light image of Raw 246.7 cells incubated with probe 3 (a and b, respectively); Chemiluminescence microscopy image and transmitted light image of Raw 246.7 cells incubated with probe 4 (c and d, respectively); Chemiluminescence microscopy image and transmitted light image of CT26 cells incubated with probe 3 (e and f, respectively); Chemiluminescence microscopy image and transmitted light image of CT26 cells incubated with probe 4 (g and h, respectively); Chemiluminescence microscopy image and transmitted light image of 3T3 cells incubated with probe 3 (i and j, respectively); Chemiluminescence microscopy image and transmitted light image of 3T3 cells incubated with probe 4 (k and l, respectively).

After the initial screening via chemiluminescence kinetics with extracellular cathepsin B, probes 3 and 4 were chosen for cell imaging evaluation. These probes were selected as they showed the highest light emission upon incubation with cathepsin B. The imaging was done with a microscope suitable for localizing and quantifying chemiluminescent signals (LV200). Raw 264.7, CT26 tumor cells, and 3T3 normal cells were incubated with either probe 3 or probe 4 and imaged using the LV200. As shown in FIG. 3, incubating with probe 4 led to both Raw 246.7 and CT26 cancer cells being imaged via the chemiluminescence signal, while no chemiluminescence signal was observed for the 3T3 cells. This correlates to the fact that Raw 246.7 and CT26 cells were found to overexpress cathepsin B, while mouse fibroblast 3T3 cells as the normal tissue cells, produce significantly lower cathepsin B levels. As such, it can be concluded that probe 4 is able to differentiate cancerous cells from normal tissue. On the other hand, incubation with probe 3 showed no chemiluminescence signal for either type of cell. This may be due to the lower solubility of probe 3 when compared to probe 4 (which can be concluded from the in vitro experiments), or the lack of tumor homing peptide which may add to probe 4's ability to encapsulate inside the cells.

Figure 4:
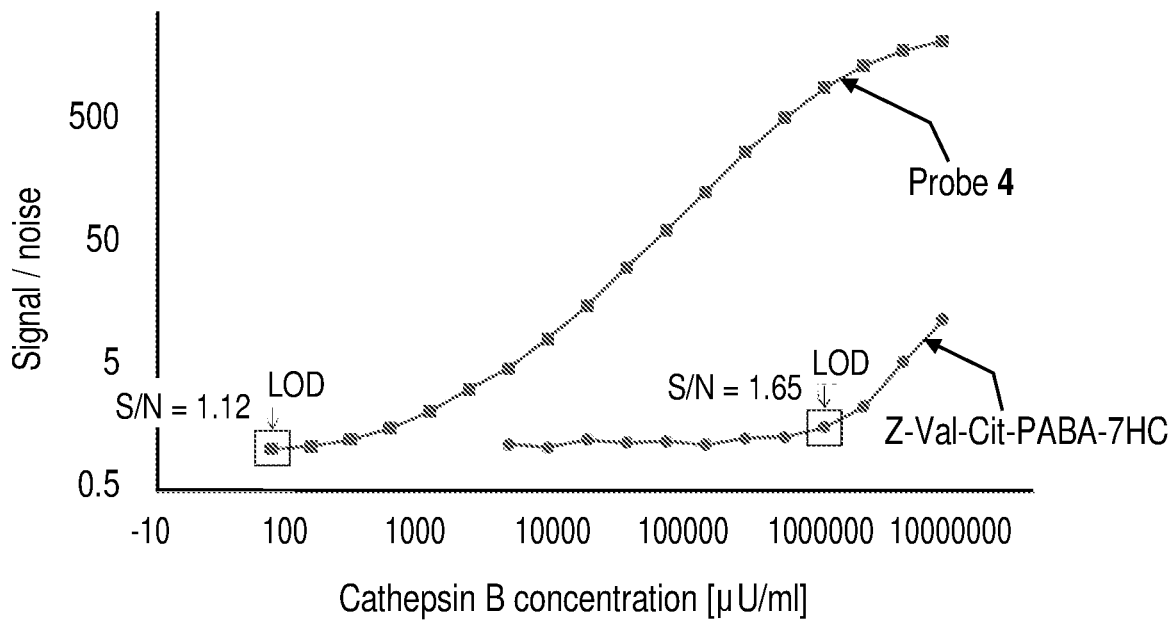
FIG. 4 shows signal/noise ratio values for probe 4 and Z-Val-Cit-PABA-7HC plotted against different cathepsin B concentrations over logarithmic scales.

The sensitivity of probe 4 to detect cathepsin B was measured and compared to that of a classic fluorescent probe (Z-Val-Cit-PABA-7HC) based on 7-hydroxy-coumarin To directly view the comparison between the two detection methods, signal/noise ratio using different cathepsin B concentrations was plotted against enzyme concentration using logarithmic scales (FIG. 4). Remarkably probe 4 exhibited a limit of detection (LOD) value of 76.29 µU/mL, while Z-Val-Cit-PABA-7HC detected cathepsin B with an LOD value of 1.25 U/mL. This superior sensitivity (more than 16,000-fold) clearly demonstrates the advantage of the chemiluminescence modality vs. fluorescence for diagnostic assays.

Study 2. Probe 5 for Use in Detection of Prostate Specific Antigen

Synthesis of Probe 5 (PSA Probe)

Compound 5a. As depicted in Scheme 15, Fmoc-Glutamine (Fmoc-Gln) (380 mg, 1.03 mmol, 1 eq) and p-aminobenzyl alcohol (133 mg, 1.08 mmol, 1.05 eq) were dissolved in THF (7 mL) and EEDQ (266.3 mg, 1.08, 1.05 eq) was added. After 16 h, the mixture was evaporated to dryness at 30° C., and the residue was triturated with ether (15 mL). The resulting off-white solid product was collected by filtration, washed with ether, and dried in vacuo (467 mg, 96%).

Compound 5b. As depicted in Scheme 15, compound 5a (250 mg, 0.525 mmol, 1 eq) was dissolved in 7 mL of ACN and cooled to 0° C. Sodium iodide (237.5 mg, 1.585 mmol, 3 eq) was added followed by the rapid addition of TMS-Cl (200 µl, 1.585 mmol, 3 eq). The reaction was allowed to warm up to room temperature and monitored by TLC (MeOH:DCM 5:95). Upon completion, the reaction mixture was diluted with EtOAc, and washed with saturated $Na_2S_2O_3$ followed by brine. The organic layer was separated, dried over $Na_2SO_4$, filtered and the solvent was evaporated under reduced pressure, to afford compound 1b (248 mg, 81% yield) as an off-white solid.

Scheme 15: Synthesis of compound 5b

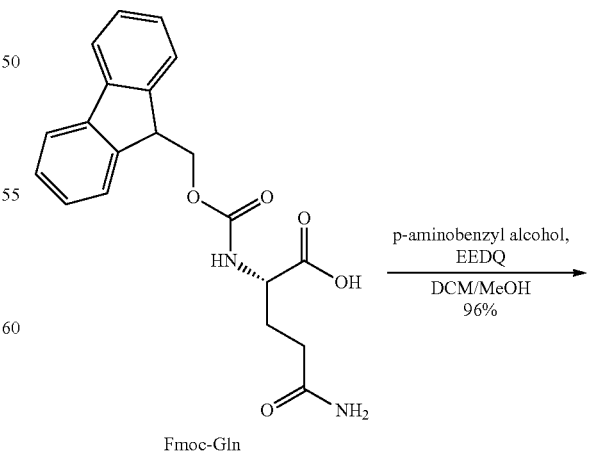

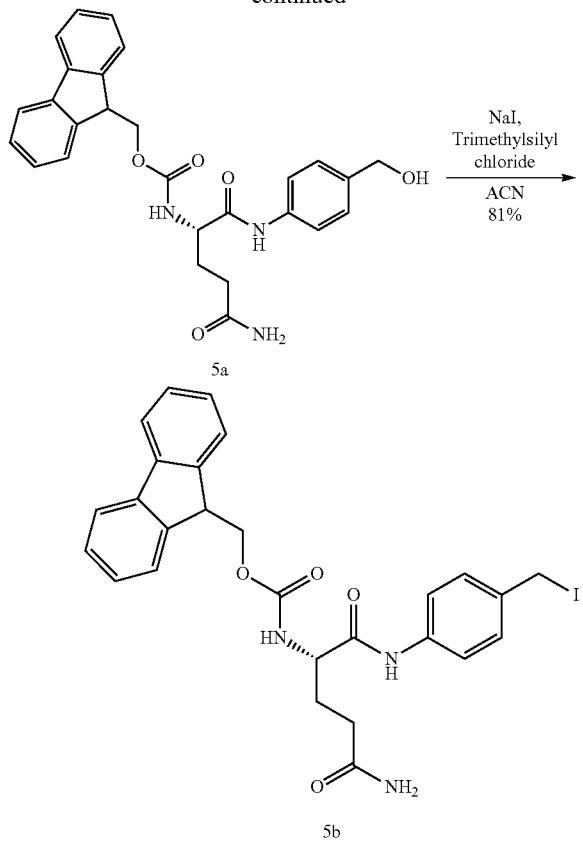

Compound 5c. As depicted in Scheme 16, compound 2a (100 mg, 0.25 mmol, 1.2 eq) was dissolved in dry DMF, under argon atmosphere and cooled to 0° C. Sodium iodide (9.23 mg, 0.23, 1.1 eq) was added, and the reaction was allowed to warm to room temperature. After stirring for 15 minutes, compound 5b (123 mg, 0.21 mmol, 1 eq) was added and the reaction was monitored by TLC (EtOAc). Upon completion, the solvent was removed under reduced pressure. The resulting oil was precipitated with 1.5 mL of EtOAc, followed by trituration with Et$_2$O (5 mL) for 10 minutes. The mixture was then filtered via vacuum filtration and the solid dried to provide compound 5c (163 mg, 92%) as an off-white solid. MS (ES–): m/z calc. for $C_{49}H_{50}ClN_3O_8$: 843.33; found: 878.64 [M+Cl]$^-$.

Compound 5d. As depicted in Scheme 16, compound 5a (110 mg, 0.13 mmol) was dissolved in 5 mL DCM. A few milligrams of methylene blue were added, and oxygen was bubbled through the solution, while irradiating with yellow light. The reaction was monitored by RP-HPLC (70-100% ACN in water, 20 min). Upon completion, the reaction mixture was concentrated by evaporation under reduced pressure and the crude product was purified by preparative RP-HPLC (70-100% ACN in water, 20 min) to afford compound 5d (72 mg, 64% yield) as a white solid.

Compound 5e. As depicted in Scheme 16, compound 5d (30 mg, 0.034 mmol) was dissolved in DMF (8 mL) and piperidine (2 mL) was added. The reaction was monitored by RP-HPLC (50-100% ACN in water, 20 min). Upon completion, the solvent was removed under reduced pressure. The resulting oil was precipitated with 1.5 mL of EtOAc, followed by trituration with Et$_2$O (20 mL) for 10 minutes. The mixture was then filtered via vacuum filtration and the solid dried to provide compound 5e (22 mg, quant.) as an off-white solid.

Scheme 16: Synthesis of compound 5e

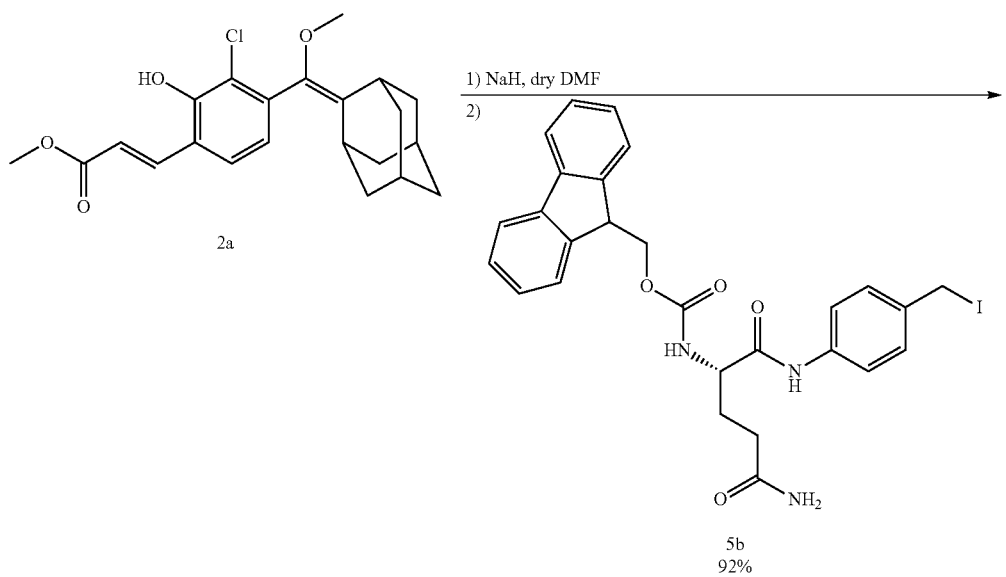

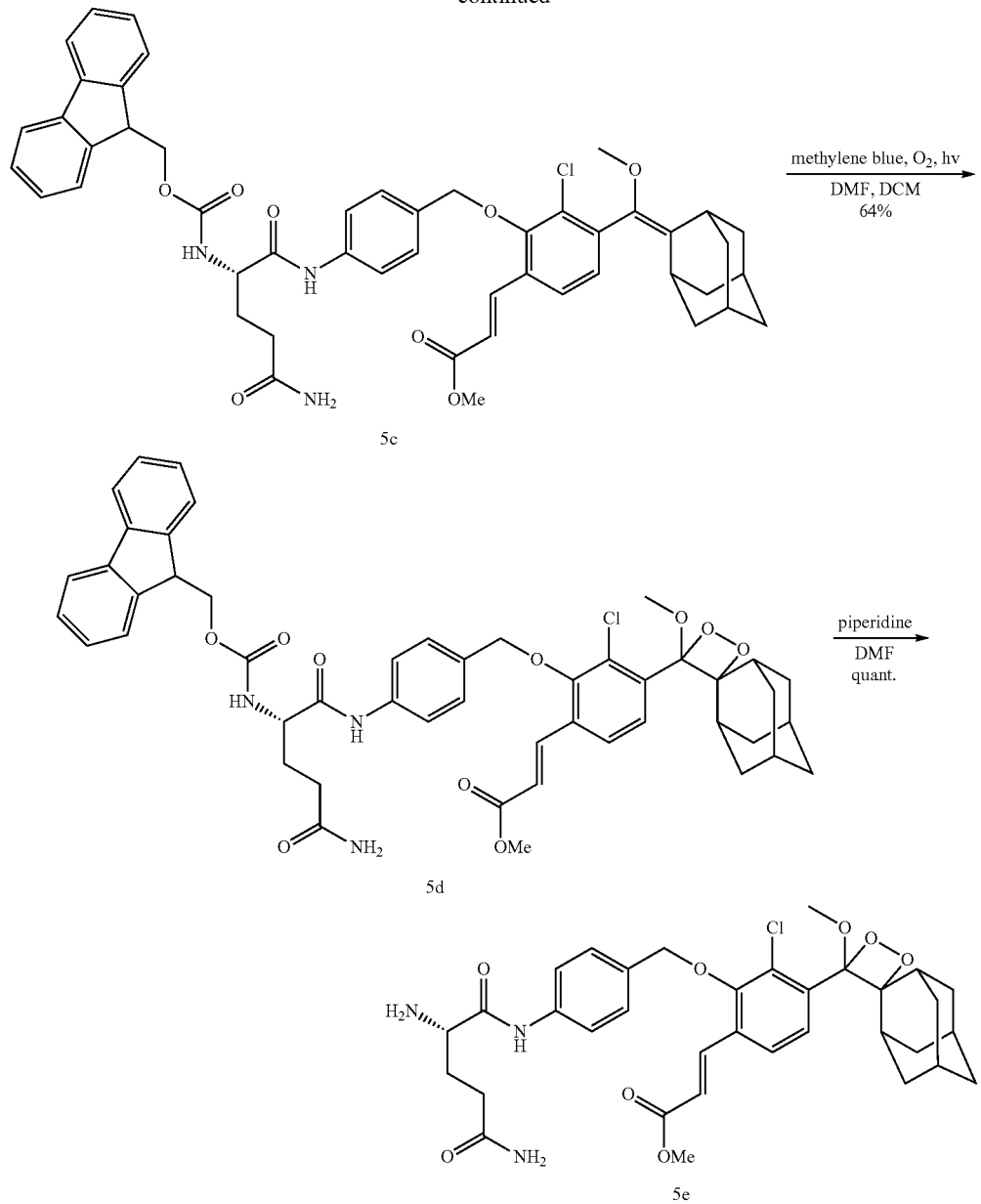

Mu-HSSKL. Peptide Mu-HSSKL (morpholino-His-Ser-Ser-Lys-Leu) was synthesized via Fmoc-Solid Phase Peptide Synthesis. Fmoc-Leu-Wang resin was swirled in DMF for 30 min. Fmoc deprotection was done with 20% piperidine (15 minutes) followed by coupling of the next amino acid (4 eq) with HBTU (4 eq) in a mixture of DIPEA (6 eq) and DMF (30 minutes). These two steps were repeated until the sequence is completed. Finally, Fmoc deprotection of the His was completed and the HSSKL sequence was coupled with 4-Morpholinecarbonyl chloride. Afterwards, the peptide was cleaved from the resin using TFA/TIPS/H$_2$O (90/5/5) solution. The peptide was precipitated and washed with cold diethyl ether solution and lyophilized. The product was afforded as a white precipitate. MS (ES−): m/z calc. for $C_{29}H_{49}N_{49}O_{10}$: 683.36; found: 682.6 [M−H]$^-$.

Compound 5f. As depicted in Scheme 17, Mu-HSSKL (175 mg, 0.25 mmol, 1 eq) was dissolved in DMF (3 mL) and Fmoc-OSu (129 mg, 0.38 mmol, 1.5 eq) and DIPEA (134 μl, 0.66 mmol, 3 eq) were added. The reaction was monitored by RP-HPLC (10-90% ACN in water, 20 min). Upon completion, the reaction mixture was concentrated by evaporation under reduced pressure and the crude product was purified by preparative RP-HPLC (10-90% ACN in water, 40 min) to afford compound 5f (162 mg, 70% yield) as a white solid. MS (ES+): m/z calc. for $C_{44}H_{59}N_9O_{12}$: 905.43; found: 906.7 [M+H]$^+$.

Compound 5g. As depicted in Scheme 17, compound 5f (10 mg, 0.0114 mmol, 1 eq) was dissolved in DMF (3 mL) and HBTU (4.8 mg, 0.0125 mmol, 1.1 eq) and DIPEA (4 μl, 0.028 mmol, 2 eq) were added. After 15 min, compound 5e (1.83 mg, 0.028 mmol, 2 eq) was added. The reaction was monitored by RP-HPLC (10-90% ACN in water, 20 min). Upon completion, the reaction mixture was concentrated by evaporation under reduced pressure and the crude product was purified by preparative RP-HPLC (10-90% ACN in water, 20 min) to afford compound 5 g (18 mg, 82% yield) as a white solid. MS (ES+): m/z calc. for $C_{78}H_{97}ClN_{12}O_{19}$: 1540.67; found: 1541.8 $[M+H]^+$.

Probe 5. As depicted in Scheme 17, compound 5 g (9 mg, 0.0057 mmol) was dissolved in 20% piperidine in DMF (1 mL). The reaction was monitored by RP-HPLC (10-90% ACN in water, 20 min). Upon completion, the solvent was removed under reduced pressure. The resulting oil was precipitated was precipitated and washed with cold diethyl ether solution and lyophilized. The product was afforded as an off-white precipitate (7 mg, quant.). MS (ES+): m/z calc. for $C_{63}H_{87}ClN_{12}O_{17}$: 1318.60; found: 1319.8 $[M+H]^+$.

In this Study, a different chemiluminescence probe, herein identified as probe 5, with a PSA cleavable peptide (HSSKLQ, histidine-serine-serine-lysin-leucin-glutamin) as a protecting group, and a 4-morpholinecarbonyl cap that is stable and supposed to increase solubility, was synthesized. The probe is based on a conventional Schaap adamantylidene-dioxetane with the addition of an elongated pi-system and an electron-withdrawing group. This donor-acceptor pair design increases the emission of the luminophore under physiological conditions, allowing it to serve as a good luminophore for one-step assays with enzymatic activation, and live-cell imaging.

Figure 5:
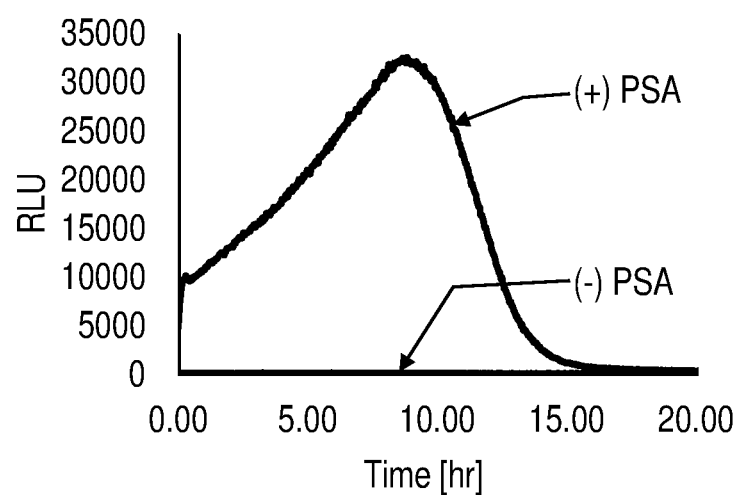
FIG. 5 shows the chemiluminescence kinetic profiles of probe 5 [10 µM] in Tris buffer (pH 7.8, 10% DMSO) in the presence of 10 mg/mL PSA at room temperature.

FIG. 5 shows the chemiluminescence kinetic profiles of probe 5 [10 μM] in Tris buffer (pH 7.8, 10% DMSO) in the presence of 10 mg/mL PSA at room temperature.

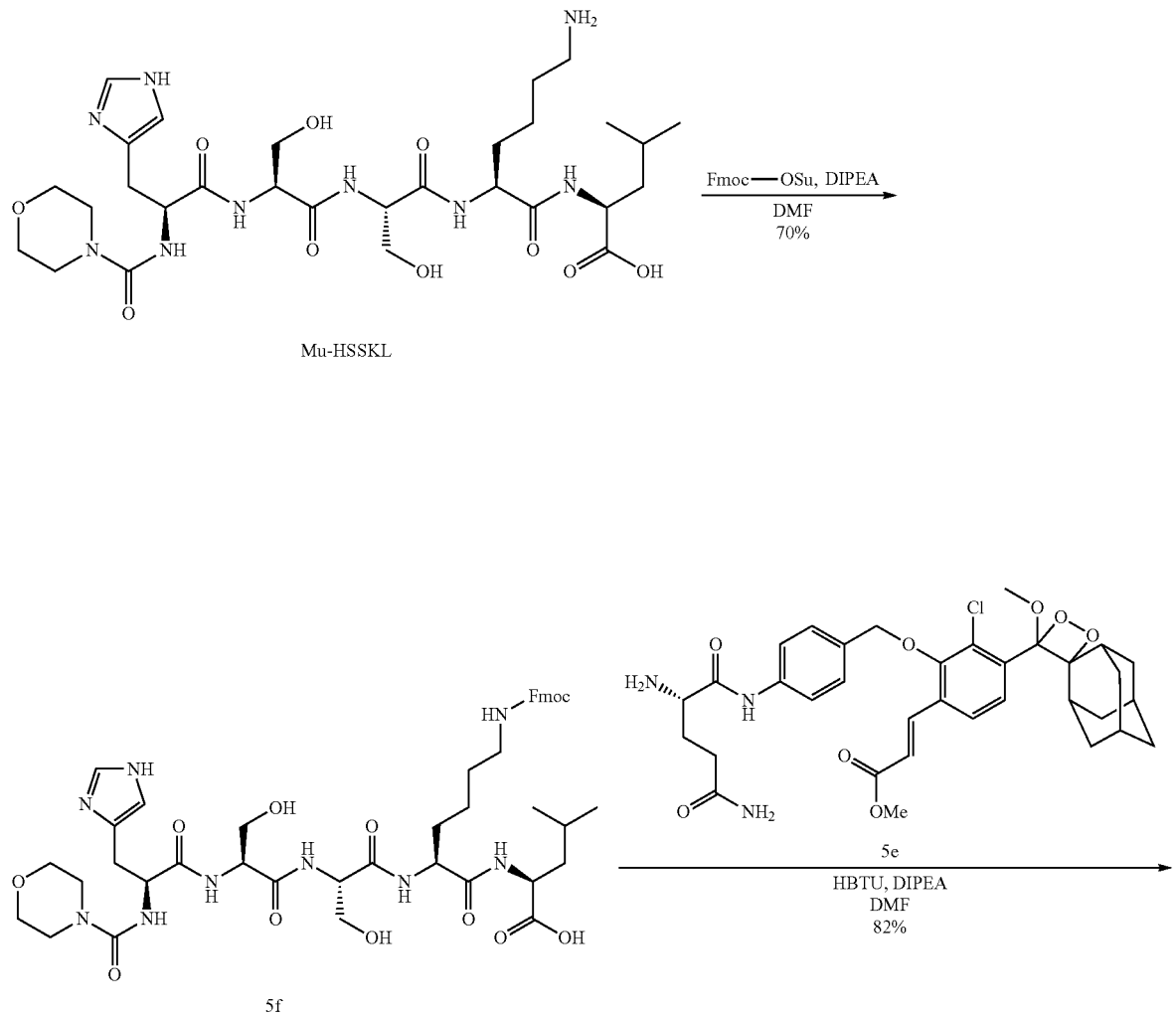

Scheme 17: Synthesis of probe 5

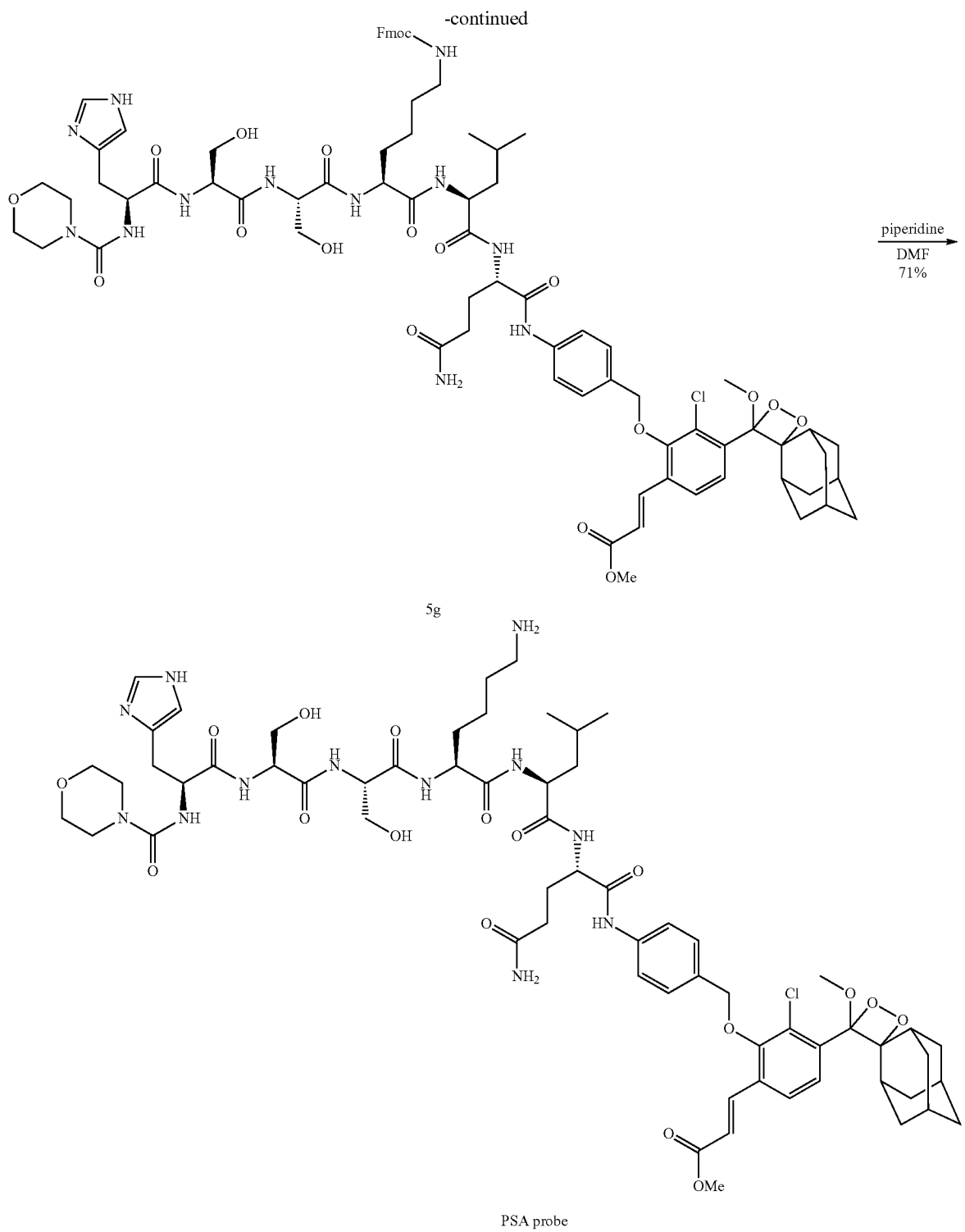

5g

PSA probe

REFERENCES

Chi, C.; Du, Y.; Ye, J.; Kou, D.; Qiu, J.; Wang, J.; Tian, J.; Chen, X. *Theranostics* 2014, 4(11), 1072-1084

Dubowchik, G. M.; Firestone, R. A.; Padilla, L.; Willner, D.; Hofstead, S. J.; Mosure, K.; Knipe, J. O.; Lasch, S. J.; Trail, P. A. *Bioconjug. Chem.* 2002, 13, 855-869

Green, O.; Eilon, T.; Hananya, N.; Gutkin, S.; Bauer, C.; Shabat, D. *ACS Cent. Sci.* 2017, 3, 349-358

Haber, G. P.; White, M. A.; Autorino, R.; Escobar, P. F.; Kroh, M. D.; Chalikonda, S.; Khanna, R.; Forest, S.; Yang, B.; Altunrende, F.; Stein, R. J.; Kaouk, J. H. *Urology* 2010, 76, 1279-1282

Ikeda, M.; Ochi, R.; Kurita, Y.; Pochan, D. J.; Hamachi, I. *Chem.-A Eur. J.* 2012, 18, 13091-13096

Mieog, J. S.; Troyan, S. L.; Hutteman, M.; Donohoe, K. J.; van der Vorst, J. R.; Stockdale, A.; Liefers, G. J.; Choi, H. S.; Gibbs-Strauss, S. L.; Putter, H.; Gioux, S.; Kuppen, P. J.; Ashitate, Y.; Lowik, C. W.; Smit, V. T.; Oketokoun, R.; Ngo, L. H.; van de Velde, C. J.; Frangioni, J. V.; Vahrmeijer, A. L. *Annals of surgical oncology* 2011, 18, 2483-2491

Miller, K.; Erez, R.; Segal, E.; Shabat, D.; Satchi-Fainaro, R. *Angew Chem Int Ed Engl.* 2009, 48(16), 2949-2954

Richard, J. A.; Jean, L.; Romieu, A.; Massonneau, M.; Noack-Fraissignes, P.; Renard, P. Y. *Org Lett.,* 2007, 9(23), 4853-4855

Segal, E.; Pan, H.; Ofek, P.; Udagawa, T.; Kopeckova, P.; Kopecek, J.; Satchi-Fainaro, R. *PLoS One* 2009, 4(4), e5233

Troyan, S. L.; Kianzad, V.; Gibbs-Strauss, S. L.; Gioux, S.; Matsui, A.; Oketokoun, R.; Ngo, L.; Khamene, A.; Azar, F.; Frangioni, J. V. *Annals of surgical oncology* 2009, 16, 2943-2952

---

What is claimed is:

1. A compound of the formula Ia or Ib:

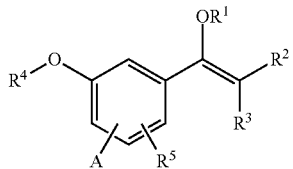

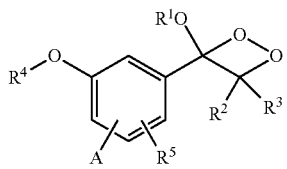

wherein $R^1$ is selected from the group consisting of a linear or branched $(C_1-C_{18})$alkyl, or $(C_3-C_7)$cycloalkyl;

$R^2$ and $R^3$ each independently is selected from the group consisting of a branched $(C_3-C_{18})$alkyl and $(C_3-C_7)$cycloalkyl, or $R_2$ and $R_3$ together with the carbon atom to which they are attached form a fused, spiro or bridged cyclic or polycyclic ring;

$R^4$ is a group of the formula:

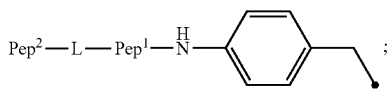

$R^5$ is H, or halogen attached either ortho or para to the $-O-R^4$ group;

A is a π* acceptor group of the formula $-CH=CH-E$, attached either ortho or para to the $-O-R^4$ group, wherein E is $-CN$, $-COOH$, $-COO(C_1-C_{18})$alkyl, 4-pyridinyl, methylpyridinium-4-yl, 3,3-dimethyl-3H-indolyl, or 1,3,3-trimethyl-3H-indol-1-ium-2-yl;

$Pep^1$ is a protease cleavable peptide moiety consisting of at least two amino acid residues and linked via a carboxylic group thereof to the aniline group, wherein said peptide moiety is protected or linked through an amino group thereof to a polyethylene glycol (PEG)-containing group;

L is absent; and $Pep^2$ is absent.

2. The compound of claim 1, wherein:
(i) $R^1$ is a linear or branched $(C_1-C_8)$alkyl; or
(ii) $R^2$ and $R^3$ together with the carbon atom to which they are attached form a fused, spiro or bridged polycyclic ring; or
(iii) $R^5$ is halogen attached ortho to the $-O-R^4$ group; or
(iv) A is $-CH=CH-E$ attached ortho to the $-O-R^4$ group, wherein E is $-CN$, $-COOH$, $-COO(C_1-C_8)$alkyl, 4-pyridinyl, methylpyridinium-4-yl, 3,3-dimethyl-3H-indolyl, or 1,3,3-trimethyl-3H-indol-1-ium-2-yl.

3. The compound of claim 2, wherein:
(i) $R^2$ and $R^3$ together with the carbon atom to which they are attached form adamantyl; or
(ii) E is $-CN$, $-COOH$, or $-COO(C_1-C_4)$alkyl.

4. The compound of claim 1, wherein:
$R^1$ is a linear or branched $(C_1-C_8)$alkyl;
$R^2$ and $R^3$ together with the carbon atom to which they are attached form a fused, spiro or bridged polycyclic ring;
$R^5$ is halogen attached ortho to the $-O-R^4$ group; and
A is $-CH=CH-E$ attached ortho to the $-O-R^4$ group, wherein E is $-CN$, $-COOH$, $-COO(C_1-C_8)$alkyl, 4-pyridinyl, methylpyridinium-4-yl, 3,3-dimethyl-3H-indolyl, or 1,3,3-trimethyl-3H-indol-1-ium-2-yl.

5. The compound of claim 4, wherein $R^1$ is methyl; $R^2$ and $R^3$ together with the carbon atom to which they are attached form adamantyl; $R^5$ is halogen attached ortho to the $-O-R^4$ group; and E is $-CN$, $-COOH$, or $-COO(C_1-C_4)$alkyl.

6. The compound of claim 5, wherein E is $-CN$, $-COOH$, $-COOCH_3$, or $-COOC(CH_3)_3$.

7. The compound of claim 1, wherein $Pep^1$ is a peptide moiety comprising or consisting of the amino acid sequence Val-Cit, Phe-Lys, Gly-Phe-Leu-Gly, Gly-Gly-Pro-Nle, Ala-Ala-Asn or His-Ser-Ser-Lys-Leu-Gln, wherein said amino acid sequence is (i) linked via the carboxylic group of the citrulline, lysine, glycine, norleucine, asparagine or glutamine, respectively, to the aniline group; and (ii) optionally protected at an amino group thereof, or linked via an amide bond and through said amino group to a PEG-containing group.

8. The compound of claim 7, wherein:
(i) said PEG-containing group is of the formula

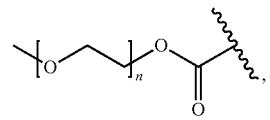

wherein n is an integer of 1 to 227; or (ii) $Pep^1$ is a peptide moiety of the sequence Val-Cit, Phe-Lys, Gly-Phe-Leu-Gly, Gly-Gly-Pro-Nle, Ala-Ala-Asn or His-Ser-Ser-Lys-Leu-Gln, linked via the carboxylic group of the citrulline, lysine, glycine, norleucine, asparagine or glutamine, respectively, to the aniline group, and protected at the α-amino group of the valine, phenylalanine, glycine, glycine, alanine or histidine, respectively, with an amino protecting group; or (iii) $Pep^1$ is a peptide moiety of the sequence Val-Cit, Phe-Lys, Gly-Phe-Leu-Gly, Gly-Gly-Pro-Nle, Ala-Ala-Asn or His-Ser-Ser-Lys-Leu-Gln, linked via the carboxylic group of the citrulline, lysine, glycine, norleucine, asparagine or glutamine, respectively, to the aniline group, and linked via the α-amino group of the valine, phenylalanine, glycine, glycine, alanine or histidine, respectively, to a PEG-containing group of the formula

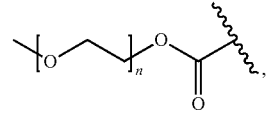

wherein n is an integer of 1 to 227.

9. The compound of claim 1, wherein $R^1$ is methyl; $R^2$ and $R^3$ together with the carbon atom to which they are attached form adamantyl; $R^5$ is Cl attached ortho to the $-O-R^4$ group; A is —CH=CH-E attached ortho to the —O—R⁴ group; E is —COOCH₃ or —CN; and (i) Pep¹ is a peptide moiety of the sequence Val-Cit, linked via the carboxylic group of the citrulline to the aniline group, and protected at the amino group of the valine with carboxybenzyl;

(ii) Pep¹ is a peptide moiety of the sequence His-Ser-Ser-Lys-Leu-Gln, linked via the carboxylic group of the glutamine to the aniline group, and protected at the α-amino group of the histidine with N-morpholinecarbonyl; or (iii) Pep¹ is a peptide moiety of the sequence Val-Cit, linked via the carboxylic group of the citrulline to the aniline group, and linked via the amino group of the valine to a PEG-containing group of the formula

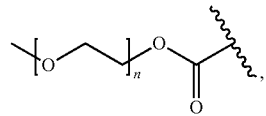

wherein n is 17.

10. The compound of claim 9, selected from the group consisting of compounds Ib-1a, Ib-1b, Ib-2a, Ib-2b, Ib-3a, and Ib-3b Ib-1a

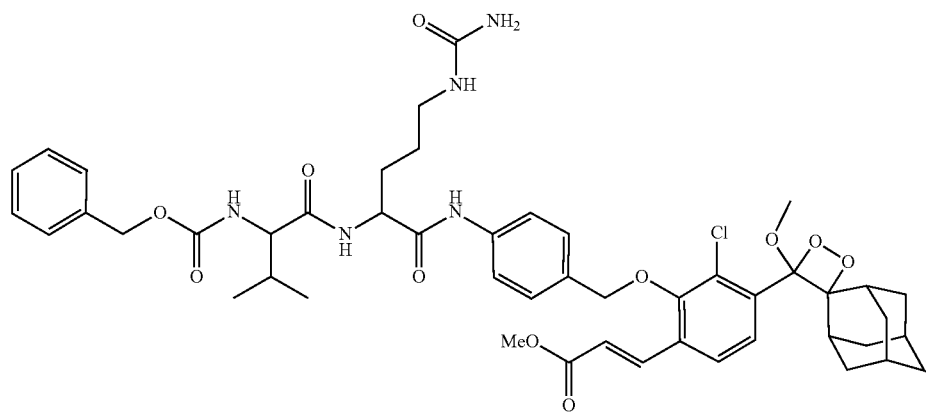

Ib-1b

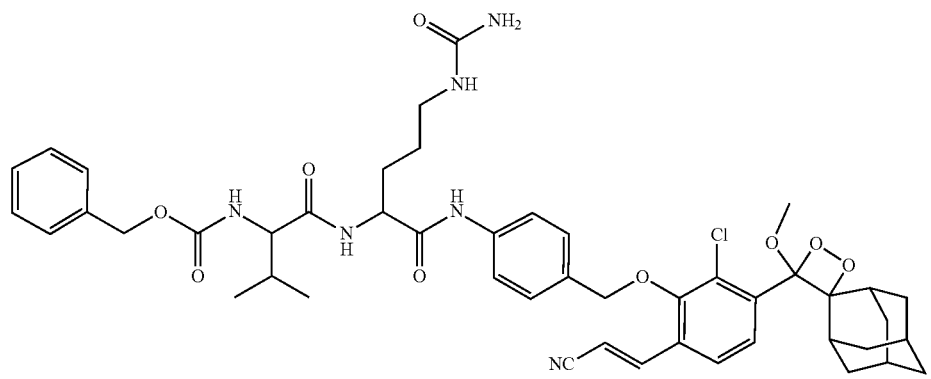

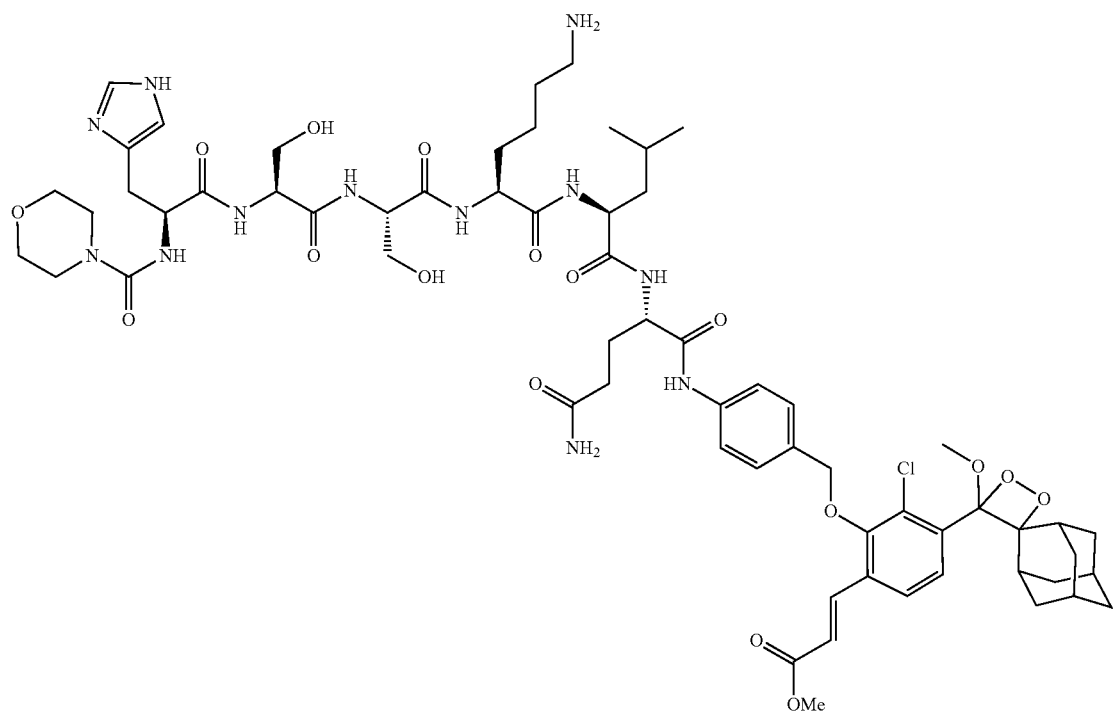
Ib-2a
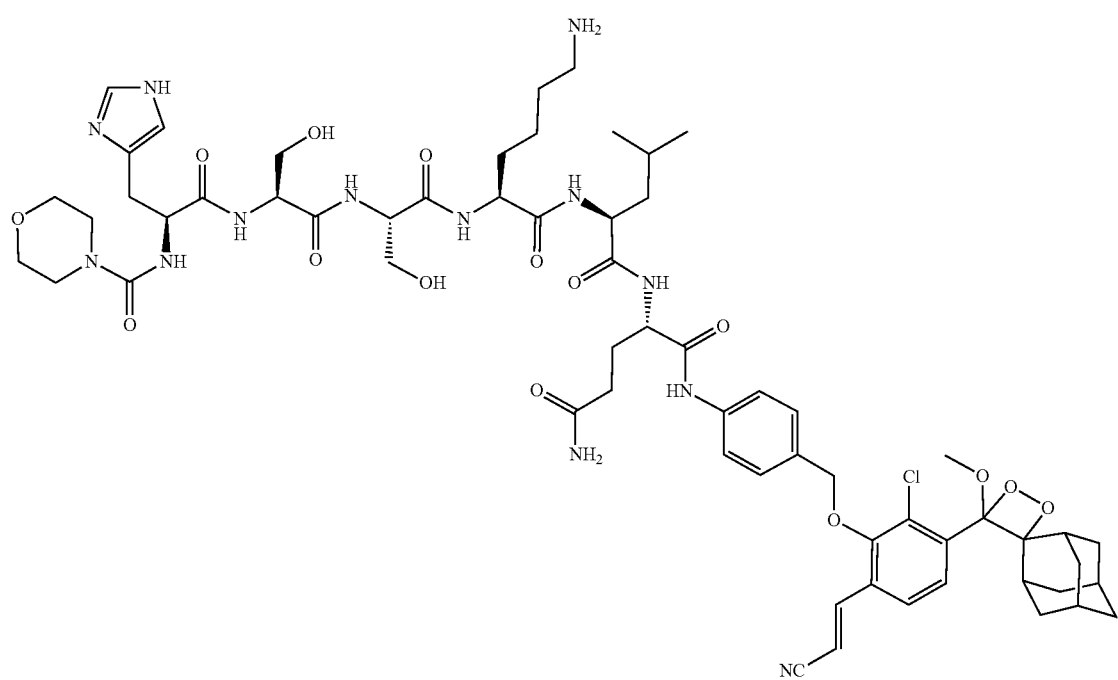
Ib-2b

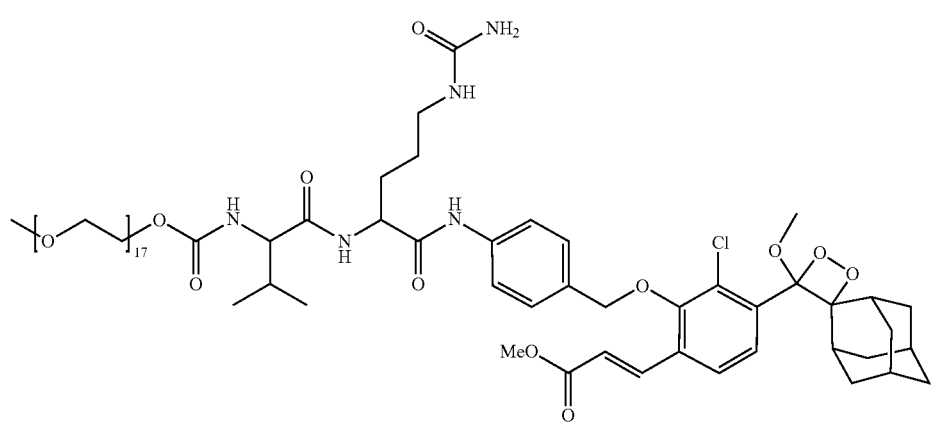

Ib-3a

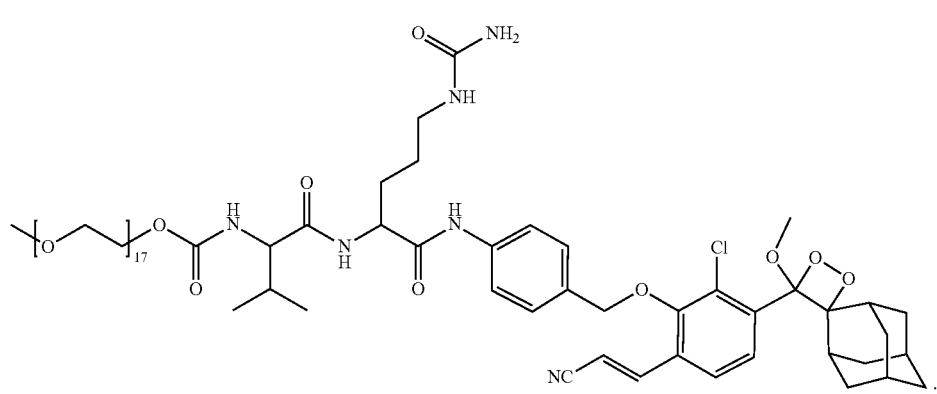

Ib-3b

11. A composition comprAising a compound according to claim 1 and a carrier.

12. A compound of the formula Ia or Ib:

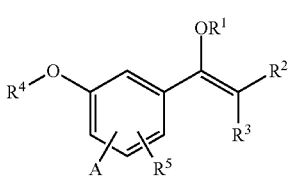

Ia

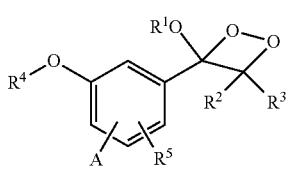

Ib wherein $R^1$ is selected from a linear or branched ($C_1$-$C_{18}$)alkyl, or ($C_3$-$C_7$)cycloalkyl;

$R^2$ and $R^3$ each independently is selected from the group consisting of a branched ($C_3$-$C_{18}$)alkyl and ($C_3$-$C_7$) cycloalkyl, or $R_2$ and $R_3$ together with the carbon atom to which they are attached form a fused, spiro or bridged cyclic or polycyclic ring;

$R^4$ is a group of the formula:

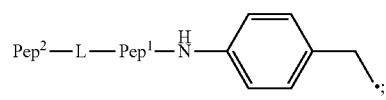

$R^5$ is H, or halogen attached either ortho or para to the —O—$R^4$ group;

A is a π* acceptor group of the formula —CH=CH-E, attached either ortho or para to the —O—$R^4$ group, wherein E is —CN, —COOH, —COO($C_1$-$C_{18}$)alkyl, 4-pyridinyl, methylpyridinium-4-yl, 3,3-dimethyl-3H-indolyl, or 1,3,3-trimethyl-3H-indol-1-ium-2-yl;

$Pep^1$ is a protease cleavable peptide moiety consisting of at least two amino acid residues and linked via a carboxylic group thereof to the aniline group;

L is a linker linked to $Pep^1$ via an amide bond through either a carboxyl or amino group of $Pep^1$; and $Pep^2$ is a cell-penetrating peptide moiety linked to L through a thiol group thereof.

13. The compound of claim 12, wherein:
(i) $R^1$ is a linear or branched ($C_1$-$C_8$)alkyl; or
(ii) $R^2$ and $R^3$ together with the carbon atom to which they are attached form a fused, spiro or bridged polycyclic ring; or
(iii) $R^5$ is halogen attached ortho to the —O—$R^4$ group; or
(iv) A is —CH=CH-E attached ortho to the —O—$R^4$ group, wherein E is —CN, —COOH, —COO($C_1$-$C_8$) alkyl, 4-pyridinyl, methylpyridinium-4-yl, 3,3-dimethyl-3H-indolyl, or 1,3,3-trimethyl-3H-indol-1-ium-2-yl.

14. The compound of claim 13, wherein:
(i) $R^2$ and $R^3$ together with the carbon atom to which they are attached form adamantyl; or
(ii) E is —CN, —COOH, or —COO($C_1$-$C_4$)alkyl.

15. The compound of claim 12, wherein:
$R^1$ is a linear or branched ($C_1$-$C_8$)alkyl;
$R^2$ and $R^3$ together with the carbon atom to which they are attached form a fused, spiro or bridged polycyclic ring;
$R^5$ is halogen attached ortho to the —O—$R^4$ group; and
A is —CH=CH-E attached ortho to the —O—$R^4$ group, wherein E is —CN, —COOH, —COO($C_1$-$C_8$)alkyl, 4-pyridinyl, methylpyridinium-4-yl, 3,3-dimethyl-3H-indolyl, or 1,3,3-trimethyl-3H-indol-1-ium-2-yl.

16. The compound of claim 15, wherein $R^1$ is methyl; $R^2$ and $R^3$ together with the carbon atom to which they are attached form adamantyl; $R^5$ is halogen attached ortho to the —O—$R^4$ group; and E is —CN, —COOH, or —COO($C_1$-$C_4$)alkyl.

17. The compound of claim 16, wherein E is —CN, —COOH, —COOCH$_3$, or —COOC(CH$_3$)$_3$.

18. The compound of claim 12, wherein Pep$^1$ is a peptide moiety comprising or consisting of the amino acid sequence Val-Cit, Phe-Lys, Gly-Phe-Leu-Gly, Gly-Gly-Pro-Nle, Ala-Ala-Asn or His-Ser-Ser-Lys-Leu-Gln, linked via the carboxylic group of the citrulline, lysine, glycine, norleucine, asparagine or glutamine, respectively, to the aniline group; and L is a linker linked to Pep$^1$ via an amide bond through either a carboxyl or amino group of Pep$^1$.

19. The compound of claim 18, wherein L is a linker of the formula:

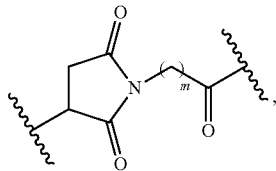

linked to Pep$^1$ via an amide bond through an amino group of Pep$^1$, wherein m is an integer of 1-20, and the alkylene chain of L is optionally interrupted with one or more —O— groups; and Pep$^2$ is a peptide moiety of the sequence Cys-Gly-Lys-Arg-Lys, linked to L through the thiol group of the cysteine residue.

20. The compound of claim 12, wherein
$R^1$ is methyl;
$R^2$ and $R^3$ together with the carbon atom to which they are attached form adamantyl;
$R^5$ is Cl attached ortho to the —O—$R^4$ group;
A is —CH=CH-E attached ortho to the —O—$R^4$ group;
E is —COOCH$_3$ or —CN;
Pep$^1$ is a peptide moiety of the sequence Val-Cit or His-Ser-Ser-Lys-Leu-Gln, linked via the carboxylic group of the citrulline or glutamine, respectively, to the aniline group;
L is a linker of the formula:

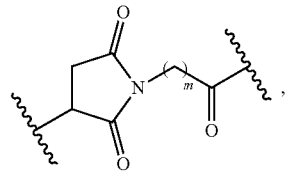

wherein m is an integer of 5, linked to Pep$^1$ via an amide bond through the α-amino group of the valine or histidine, respectively; and Pep$^2$ is a peptide moiety of the sequence Cys-Gly-Lys-Arg-Lys, linked to L through the thiol group of the cysteine residue.

21. The compound of claim 20, selected from the group consisting of compounds Ib-4a, Ib-4b, Ib-5a, and Ib-5b

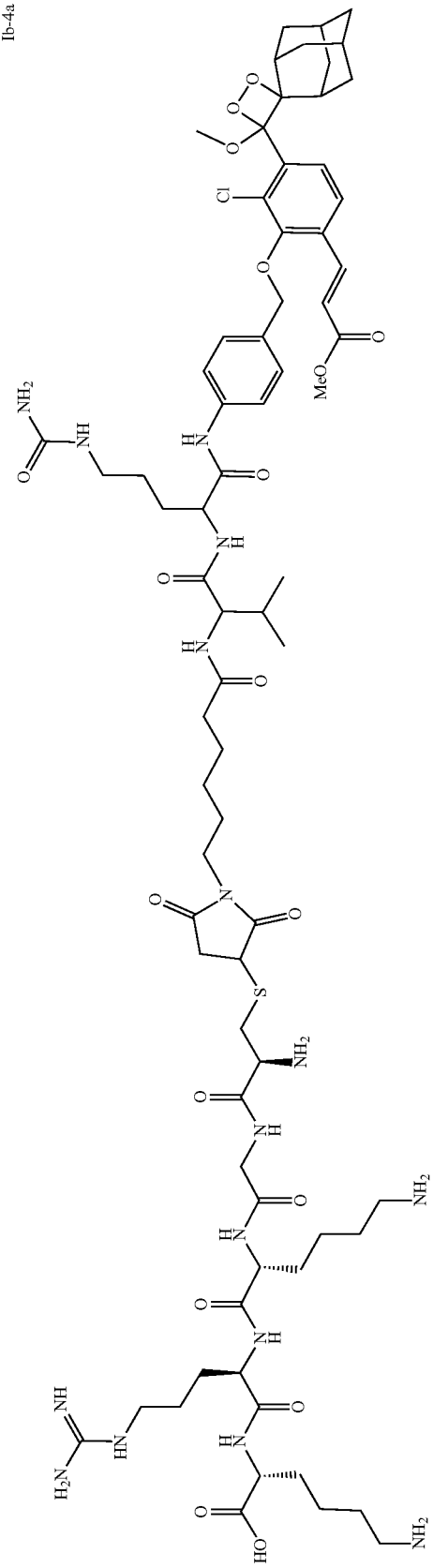
Ib-4a
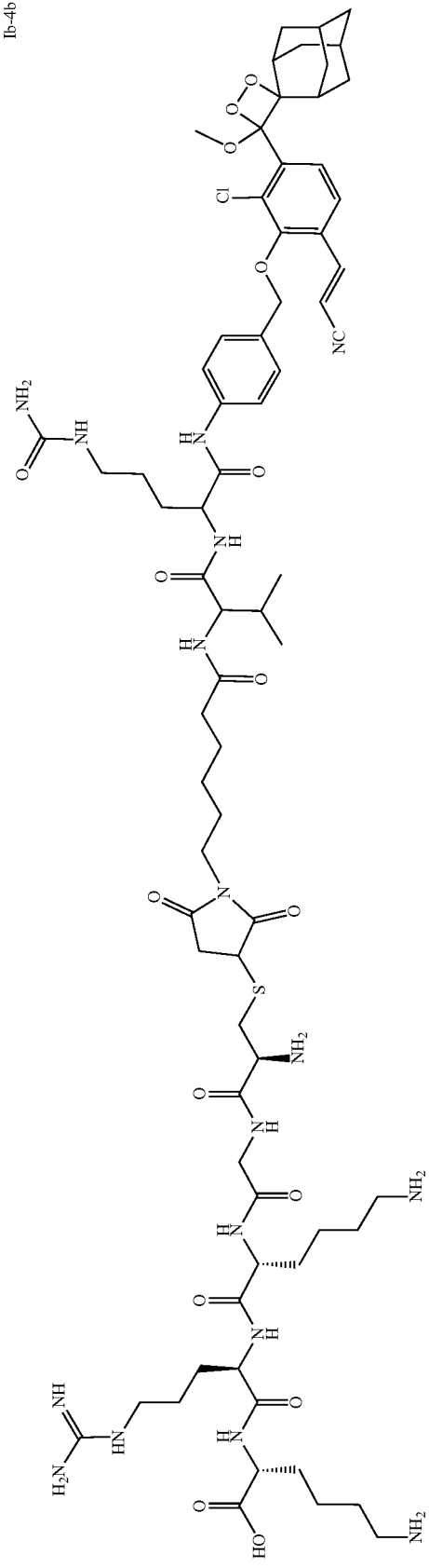
Ib-4b

Ib-5a
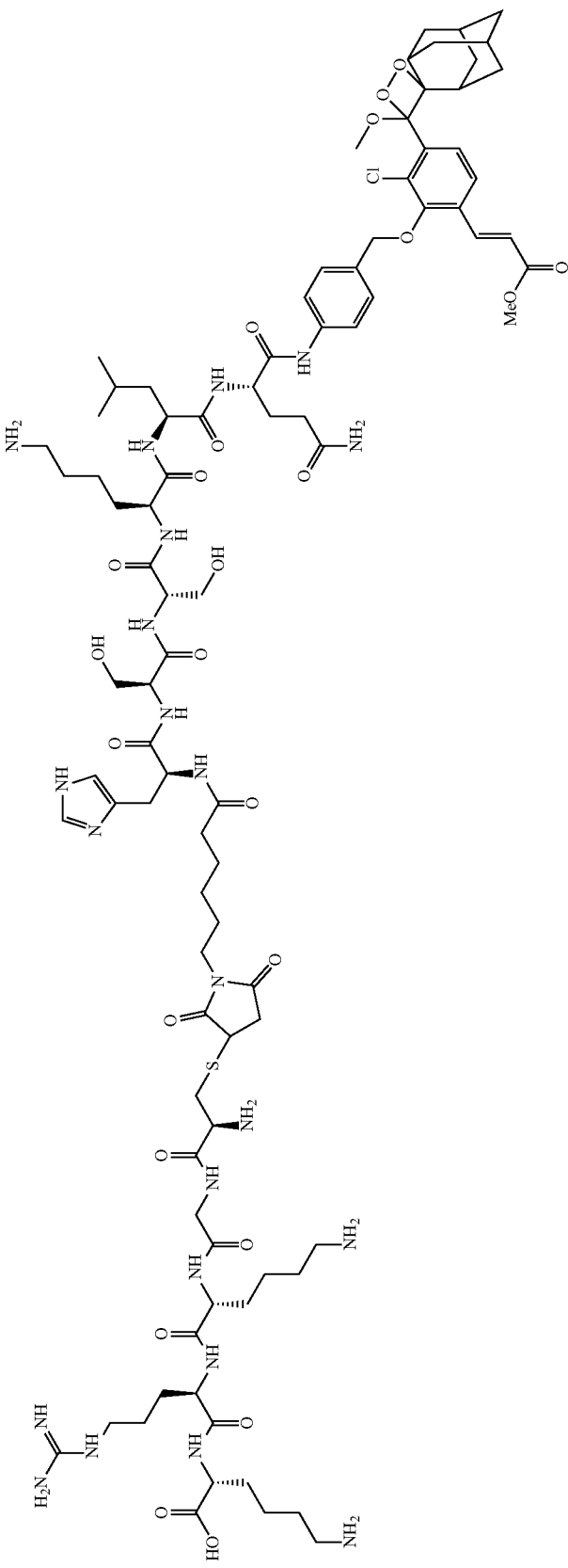

Ib-5b
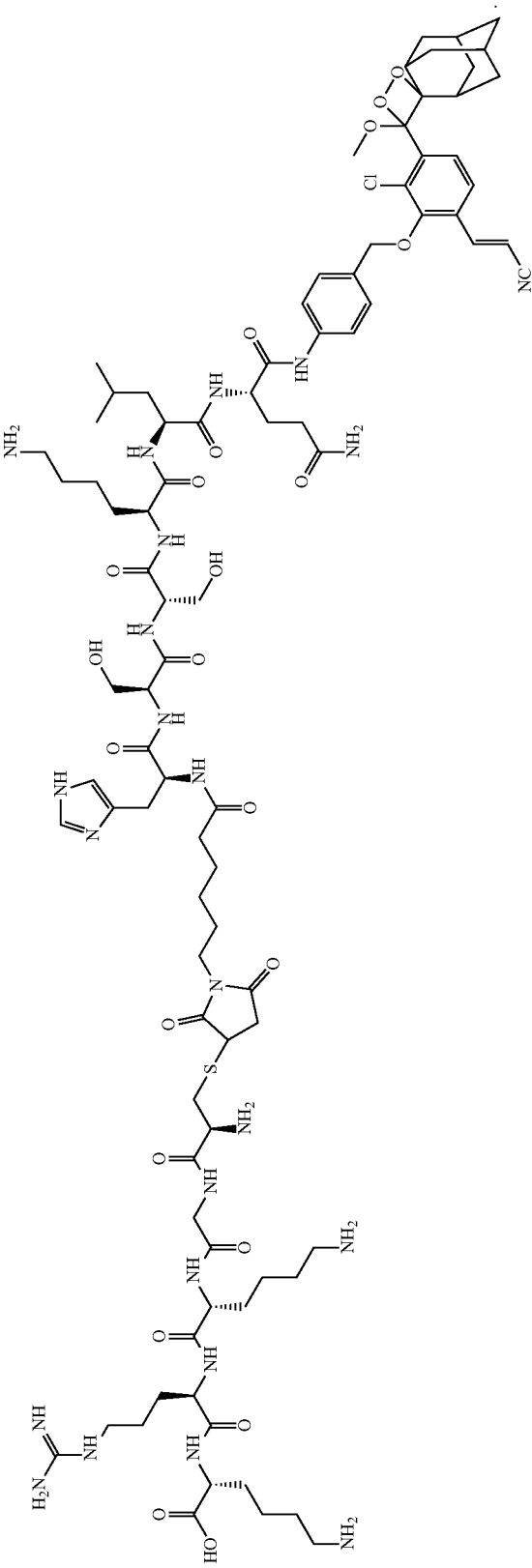

22. A composition comprising a compound according to claim 12 and a carrier.

\* \* \* \* \*

UNITED STATES PATENT AND TRADEMARK OFFICE
CERTIFICATE OF CORRECTION

PATENT NO. : 12,173,350 B2
APPLICATION NO. : 16/616356
DATED : December 24, 2024
INVENTOR(S) : Doron Shabat et al.

It is certified that error appears in the above-identified patent and that said Letters Patent is hereby corrected as shown below:

On the Title Page

Item (56), Column 2, Line 3, delete "Green, ACX Central" and insert --Green, ACS Central--.

Item (56), Column 2, Line 12, delete "al; "CelL-penetrating" and insert --al; "Cell-penetrating--.

In the Specification

In Column 4, Line 8, delete "strong chemiliminescent" and insert --strong chemiluminescent--.

In Column 4, Line 34 (Approx.), delete "or ($C_3$-C7)cycloalkyl," and insert --or ($C_3$-$C_7$)cycloalkyl,--.

In Column 5, Lines 42-43 (Approx.), delete "and chemilluminescence imaging" and insert --and chemiluminescence imaging--.

In Column 6, Line 9, delete "isobutyl, tent-butyl," and insert --isobutyl, tert-butyl,--.

In Column 6, Line 44, delete "glutamine (Gin), glycine" and insert --glutamine (Gln), glycine--.

In Column 6, Lines 51-52, delete "γ-aminobutiric acid (GABA)," and insert --γ-aminobutyric acid (GABA),--.

In Column 6, Line 53, delete "p-propargly-oxy-phenylalanine," and insert --p-propargyl-oxy-phenylalanine,--.

In Column 7, Line 24 (Approx.), delete "in Green and" and insert --in Greene and--.

In Column 7, Line 32 (Approx.), delete "(DMPM), p- methoxyphenyl (PMP)," and insert --(DMPM), p-methoxyphenyl (PMP),--.

Signed and Sealed this
Third Day of June, 2025

Coke Morgan Stewart
*Acting Director of the United States Patent and Trademark Office*

CERTIFICATE OF CORRECTION (continued)
U.S. Pat. No. 12,173,350 B2

In Column 7, Line 4 (Approx.) (TABLE 1), delete "4-piridinyl" and insert --4-pyridinyl--.

In Column 7, Line 4 (Approx.) (TABLE 1), delete "methylpiridinium-4-yl" and insert --methylpyridinium-4-yl--.

In Column 10, Line 14 (Approx.), delete "Leu-Gly, (SEQ" and insert --Leu-Gly (SEQ--.

In Column 10, Line 15 (Approx.), delete "Pro-Nle, (SEQ" and insert --Pro-Nle (SEQ--.

In Column 10, Lines 39-40, delete "phenylalanine, glycine, glycine, alanine" and insert --phenylalanine, glycine, alanine--.

In Column 10, Lines 49-50, delete "phenylalanine, glycine, glycine, alanine" and insert --phenylalanine, glycine, alanine--.

In Column 10, Line 65, delete "Leu-Gly, (SEQ" and insert --Leu-Gly (SEQ--.

In Column 10, Line 67, delete "Leu-Gln, (SEQ" and insert --Leu-Gln (SEQ--.

In Column 19, Line 3, delete "in Remington: The" and insert --in Remington. The--.

In Column 19, Line 59 (Approx.), delete "graft surgery: The" and insert --graft surgery. The--.

In Column 20, Line 36, delete "MHz. $^1$C-NMR spectra" and insert --MHz. $^{13}$C-NMR spectra--.

In Column 33, Line 64, delete "MHz, CDCl3)" and insert --MHz, CDCl$_3$)--.

In Column 38, Line 57, delete "Hz, 3H).$^3$C" and insert --Hz, 3H).$^{13}$C--.

In Column 39, Line 55 (Approx.), delete "(Hamamatsu C$_{9100}$-13). RAW" and insert --(Hamamatsu C9100-13). RAW--.

In Column 42, Line 3, delete "7-hydroxy-coumarin" and insert --7-hydroxy-coumarin.--.

In Column 44, Line 34 (Approx.), delete "compound Se (22" and insert --compound 5e (22--.

In Column 45, Line 65, delete "C$_{29}$H$_{49}$N$_{49}$O$_{10}$: 683.36;" and insert --C$_{29}$H$_{49}$N$_9$O$_{10}$: 683.36;--.

In Column 48, Line 1, delete "serine-lysin-leucin-glutamin) as" and insert --serine-lysine-leucine-glutamine) as--.

In the Claims

In Column 53, Claim 1, Line 23 (Approx.), delete "(C$_1$-C$_{18}$)alkyl, or (C$_3$-C$_7$)" and insert --(C$_1$-C$_{18}$)alkyl, and (C$_3$-C$_7$)--.

CERTIFICATE OF CORRECTION (continued)
U.S. Pat. No. 12,173,350 B2

In Column 54, Claim 7, Line 24 (Approx.), delete "and (ii) optionally" and insert --and (ii)--.

In Column 59, Claim 11, Line 36 (Approx.), delete "composition comprAising a" and insert --composition comprising a--.

SEQUENCE LISTING

```
<160> NUMBER OF SEQ ID NOS: 4

<210> SEQ ID NO 1
<211> LENGTH: 4
<212> TYPE: PRT
<213> ORGANISM: Artificial Sequence
<220> FEATURE:
<223> OTHER INFORMATION: synthetic peptide

<400> SEQUENCE: 1

Gly Phe Leu Gly
1

<210> SEQ ID NO 2
<211> LENGTH: 4
<212> TYPE: PRT
<213> ORGANISM: Artificial Sequence
<220> FEATURE:
<223> OTHER INFORMATION: synthetic peptide
<220> FEATURE:
<221> NAME/KEY: VARIANT
<222> LOCATION: (4)..(4)
<223> OTHER INFORMATION: Xaa = norleucine (Nle)

<400> SEQUENCE: 2

Gly Gly Pro Xaa
1

<210> SEQ ID NO 3
<211> LENGTH: 6
<212> TYPE: PRT
<213> ORGANISM: Artificial Sequence
<220> FEATURE:
<223> OTHER INFORMATION: synthetic peptide

<400> SEQUENCE: 3

His Ser Ser Lys Leu Gln
1               5

<210> SEQ ID NO 4
<211> LENGTH: 5
<212> TYPE: PRT
<213> ORGANISM: Artificial Sequence
<220> FEATURE:
<223> OTHER INFORMATION: synthetic peptide

<400> SEQUENCE: 4

Cys Gly Lys Arg Lys
1               5
```